United States Patent
Thorner et al.

(10) Patent No.: US 11,248,216 B2
(45) Date of Patent: Feb. 15, 2022

(54) METHODS AND COMPOSITIONS FOR GENOMIC EDITING

(71) Applicant: The Regents of the University of California, Oakland, CA (US)

(72) Inventors: Jeremy W. Thorner, Berkeley, CA (US); Gregory Charles Finnigan, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 574 days.

(21) Appl. No.: 16/090,119

(22) PCT Filed: Apr. 20, 2017

(86) PCT No.: PCT/US2017/028676
§ 371 (c)(1),
(2) Date: Sep. 28, 2018

(87) PCT Pub. No.: WO2017/189336
PCT Pub. Date: Nov. 2, 2017

(65) Prior Publication Data
US 2019/0194632 A1  Jun. 27, 2019

Related U.S. Application Data

(60) Provisional application No. 62/327,141, filed on Apr. 25, 2016.

(51) Int. Cl.
| | |
|---|---|
| *C12N 9/22* | (2006.01) |
| *C12N 15/90* | (2006.01) |
| *C12N 15/09* | (2006.01) |
| *C12N 15/79* | (2006.01) |
| *C12N 15/10* | (2006.01) |
| *C12N 15/11* | (2006.01) |
| *C12N 15/81* | (2006.01) |

(52) U.S. Cl.
CPC ............ *C12N 9/22* (2013.01); *C12N 15/09* (2013.01); *C12N 15/102* (2013.01); *C12N 15/11* (2013.01); *C12N 15/79* (2013.01); *C12N 15/81* (2013.01); *C12N 15/90* (2013.01); *C12N 2310/20* (2017.05)

(58) Field of Classification Search
CPC ......... C12N 9/22; C12N 15/905; C12N 15/81
See application file for complete search history.

(56) References Cited

U.S. PATENT DOCUMENTS

| | | |
|---|---|---|
| 2014/0090113 A1 | 3/2014 | Cogan et al. |
| 2015/0159174 A1 | 6/2015 | Frendewey et al. |

OTHER PUBLICATIONS

Finnigan, et al.; "mCAL: A New Approach for Versatile Multiplex Action of Cas9 Using One sgRNA and Loci Flanked by a Programmed Target Sequence"; Genes Genomes Genetics; vol. 6, pp. 2147-2156 (Jul. 2016).

Schumacher, et al.; "Multiplexed GuideRNA-expression to Efficiently Mutagenize Multiple Loci in *Arabidopsis* by CRISPR-Cas9"; Bio-Protocol; vol. 7, No. 5, 14 pages (Mar. 5, 2017).

*Primary Examiner* — Suzanne M Noakes
(74) *Attorney, Agent, or Firm* — Bozicevic Field & Francis, LLP; Paula A. Borden; Mandar Joshi

(57) ABSTRACT

The present disclosure provides genetically modified cells and non-human organisms, and methods of producing such cells and organisms. Also provided are methods of editing the genome of such cells and organisms. The cells and non-human organisms of the disclosure are genetically modified such that their genome includes an integrated heterologous nucleic acid (that includes a CRISPR/Cas target sequence) at one or more (e.g., 2 or more, 3 or more, 4 or more, etc.) positions within the genome. The integrated nucleic acids, which include the same CRISPR/Cas target sequence, allow for simultaneous gene editing at multiple different positions within a genome using a single species of CRISPR/Cas guide RNA (i.e., one guide RNA will target multiple sites because the multiple sites have the same target sequence).

19 Claims, 17 Drawing Sheets

Specification includes a Sequence Listing.

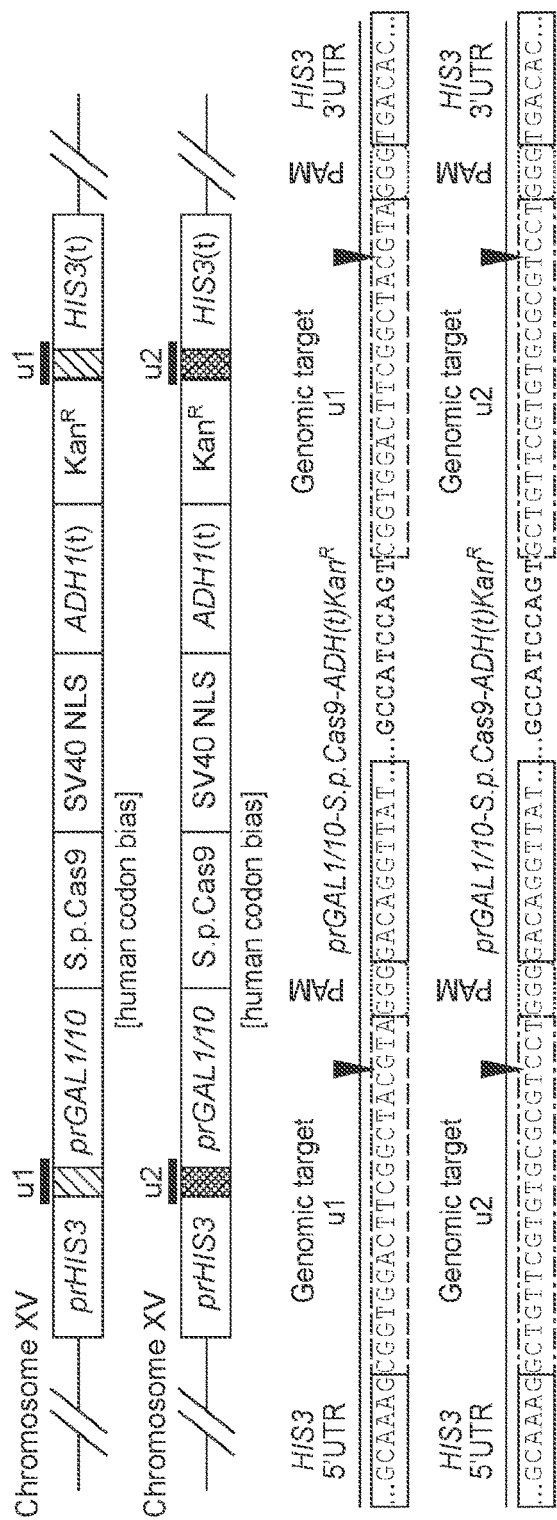

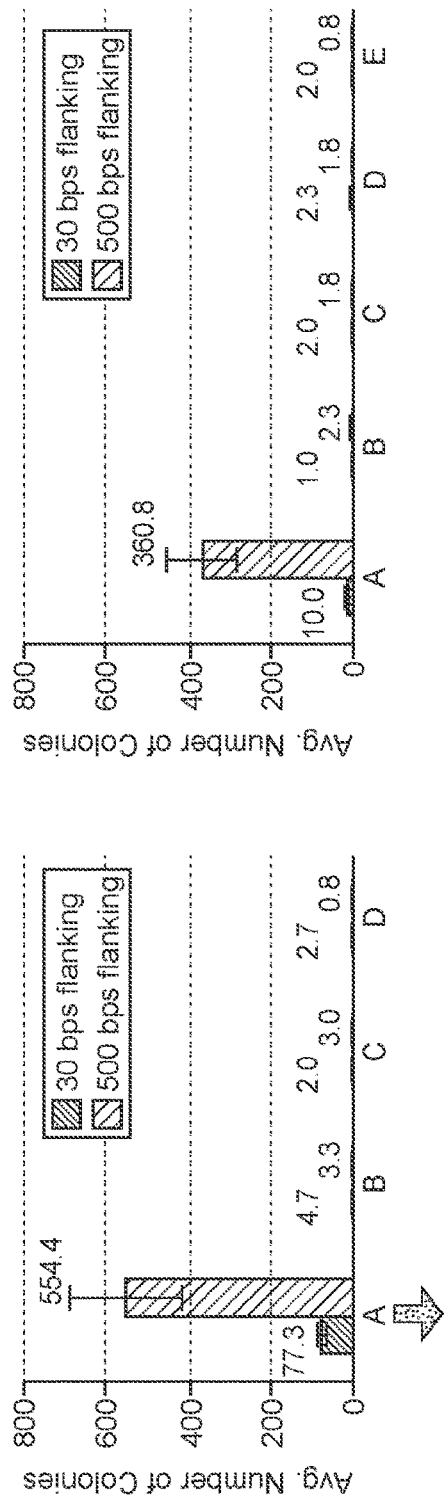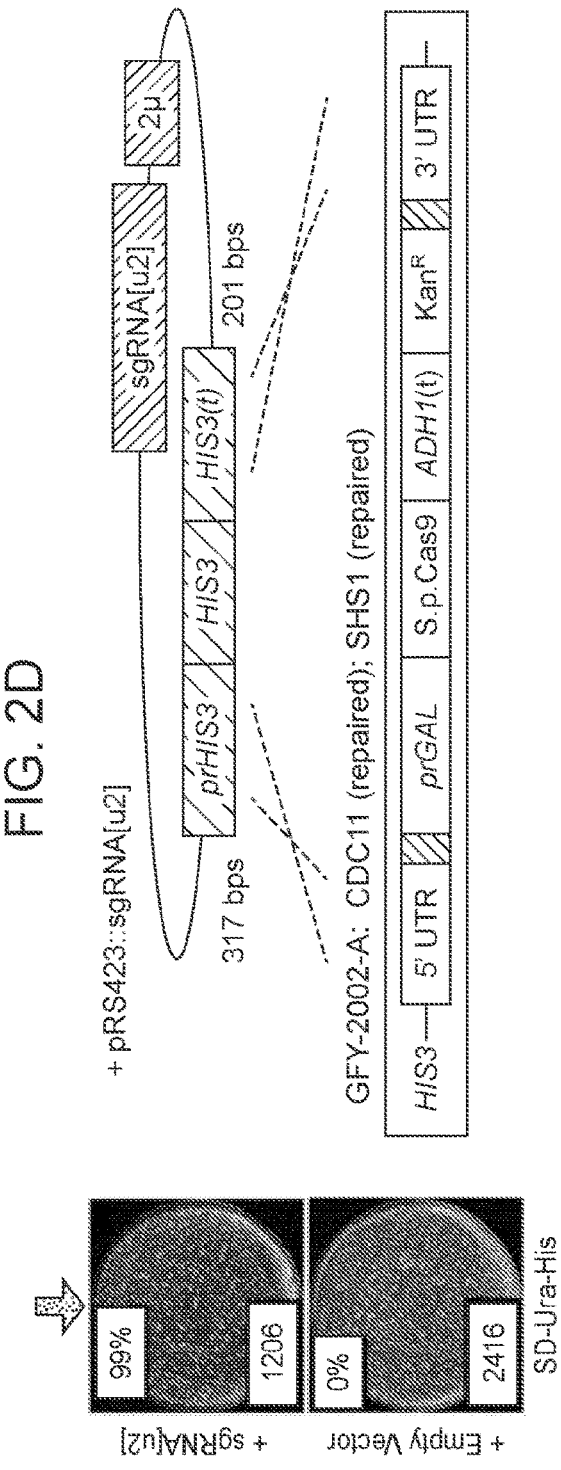

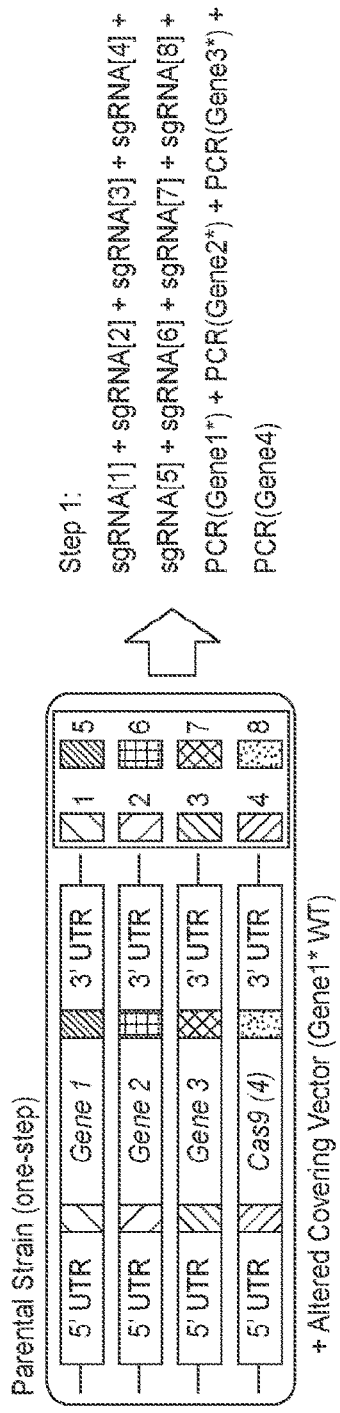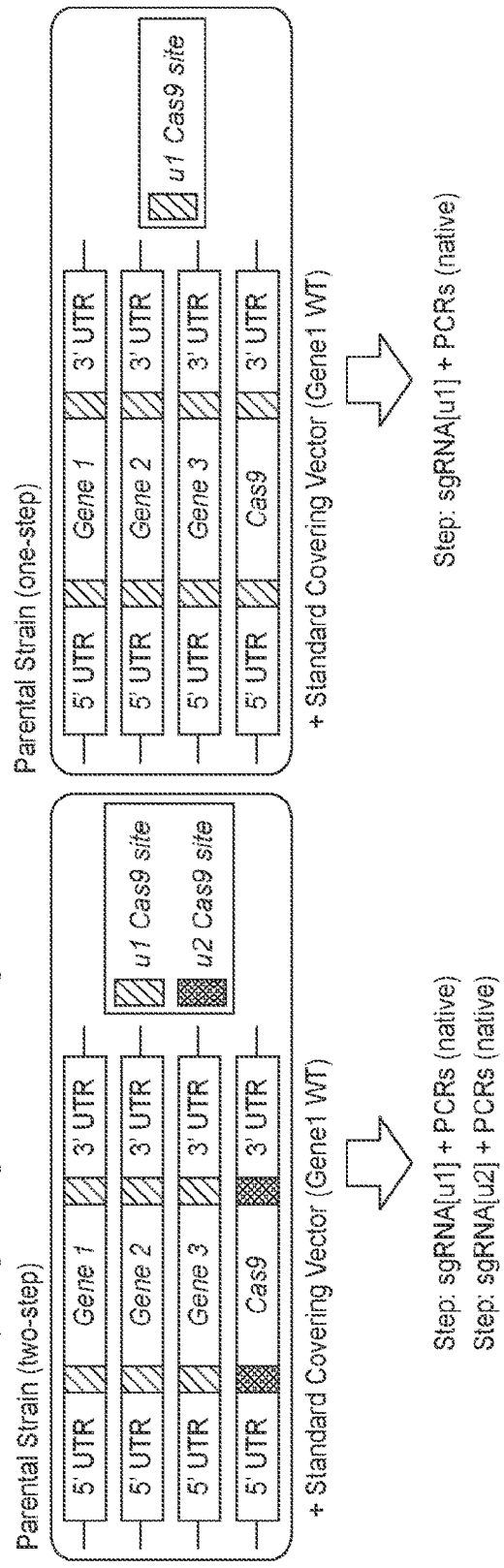
FIG. 4A
FIG. 4B

METHODS AND COMPOSITIONS FOR GENOMIC EDITING

CROSS-REFERENCE

This application claims the benefit of U.S. Provisional Patent Application No. 62/327,141, filed Apr. 25, 2016, which application is incorporated herein by reference in its entirety.

STATEMENT REGARDING FEDERALLY SPONSORED RESEARCH

This invention was made with government support under Grant No. GM021841 and GM101314 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-328WO_Seq_List_ST25.txt" created on Apr. 13, 2017 and having a size of 7,899 KB. The contents of the text file are incorporated by reference herein in their entirety.

INTRODUCTION

The CRISPR/Cas (Clustered Regularly-Interspaced Short Palindromic Repeats) system (e.g., CRISPR/Cas9), involved in bacteria immunity has been recognized and adapted to be utilized as a powerful, programmable gene editing tool within numerous organisms. Expression of the bacterial Cas9 nuclease, as well as a short stretch of RNA containing genomic targeting information (e.g., a 20 bp sequence) and a structural component to associate with Cas9 itself, allow for the precise placement of a double stranded or single stranded break (DSB or SSB) at a desired location(s) within a genome of interest. A DSB can be repaired via homologous recombination (often from amplified polymerase chain reaction (PCR) fragments or vectors) to create a modification (deletion, addition, allele insertion, etc.) with high precision and efficiency. This strategy has been demonstrated in the creation and editing of bacterial genomes, model and non-model fungal species, zebrafish, worms, flies, plants, and human cells, and the list continues to expand rapidly. Moreover, Cas9 has also been adopted for use in a range of biological processes from mitotic gene drives to transcriptional regulators and protein scaffolds, as the guide RNA can be modified to recruit and bind additional protein factors at specific genomic positions.

There is a need in the art for improved methods and compositions for targeting multiple loci within a target genome.

SUMMARY

The present disclosure provides genetically modified cells, genetically modified non-human organisms, and methods of producing such cells and organisms. Also provided are methods of editing the genome of such cells and organisms. The genetically modified cells and non-human organisms of the disclosure are genetically modified such that their genome includes an integrated heterologous nucleic acid (that includes a CRISPR/Cas target sequence) at one or more positions within the genome, e.g., the same target sequence can be integrated at multiple different positions. In some cases, the same CRISPR/Cas target sequence is integrated into 2 or more positions within the genome (e.g., flanking a gene sequence or transcription control element; integrated within two different genes; and the like). In some cases, the same CRISPR/Cas target sequence is integrated into 3 or more (e.g., 4 or more, 5 or more, 6 or more, etc.) positions within the genome. The integrated nucleic acids, which include the same CRISPR/Cas target sequence, allow for simultaneous gene editing at multiple different positions within a genome using a single species of CRISPR/Cas guide RNA (i.e., one guide RNA will target multiple sites because the multiple sites have the same target sequence).

In some cases, the CRISPR/Cas target sequence is heterologous to the genome because the sequence is present nowhere in the genome except for where the nucleic acid has integrated. In some cases, the CRISPR/Cas target sequence is heterologous in the sense that it is found elsewhere in the genome, but is not normally present at the position the nucleic acid has integrated.

BRIEF DESCRIPTION OF THE DRAWINGS

FIG. 1 (Panel A): CDC11, left side: SEQ ID NO: 1142; CDC11, right side: SEQ ID NO: 1143; SHS1, left side: SEQ ID NO: 1144; SHS1, right side: SEQ ID NO: 1145. FIG. 1 (Panel B): HIS3 (u1), left side: SEQ ID NO: 1146; HIS3 (u1), right side: SEQ ID NO: 1147; HIS3 (u2), left side: SEQ ID NO: 1148; HIS3 (u2), right side: SEQ ID NO: 1149. FIG. 1 (Panel C): top to bottom: SEQ ID NOs.:1150-1151.

FIG. 4 (panels A-B) present a model for Cas9-mediated gene manipulation by multiplexing of the genomic target site rather than multiplexing the guide RNA.

FIG. 5 (panel B): top to bottom: SEQ ID NOs. 1152-1155.

DEFINITIONS

Figure 1A:
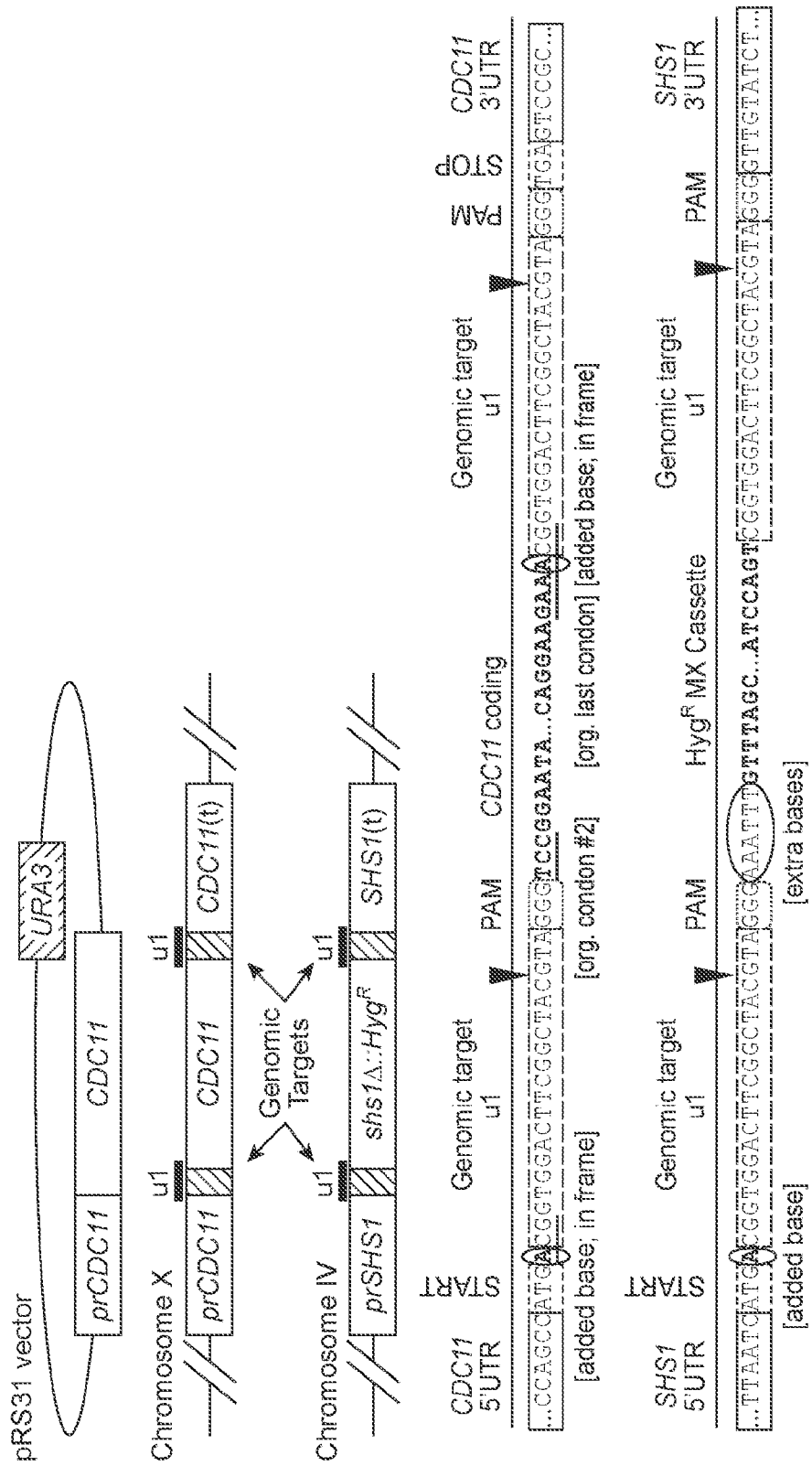
FIG. 1 (panels A-C) present schematic illustrations of programmed non-yeast Cas9 target sites at multiple loci in budding yeast.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include single-stranded and double-stranded polynucleotides.

The terms "peptide," "polypeptide," and "protein" are used interchangeably herein, and refer to a polymeric form of amino acids of any length, which can include coded and/or non-coded amino acids, chemically or biochemically modified or derivatized amino acids, and polypeptides having modified peptide backbones.

The term "naturally-occurring" as used herein as applied to a nucleic acid, a protein, a cell, or an organism, refers to a nucleic acid, protein, cell, or organism that is found in nature. For example, a polypeptide or polynucleotide sequence that is present in an organism (including viruses) that can be isolated from a source in nature and which has not been intentionally modified by a human in the laboratory is naturally occurring.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide (e.g., RuvCI, RuvCII, and RuvCIII of a Cas9 protein can form a RuvC domain).

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

"Heterologous," as used herein, means a nucleotide or polypeptide sequence that is not found in the native nucleic acid or protein, respectively (at least not at that particular position, e.g., see below). For example, in some cases, the heterologous nucleic acid (and/or the CRISPR/Cas target sequence) is heterologous to the genome because the sequence is present nowhere in the genome except for where the nucleic acid has integrated. In some cases the heterologous nucleic acid (and/or the CRISPR/Cas target sequence) is heterologous in the sense that it is found elsewhere in the genome, but is not normally present at the position the nucleic acid has (or will be) integrated.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) or protein is the product of various combinations of cloning, restriction, and/or ligation steps resulting in a construct having a sequence (e.g., structural, coding, or non-coding sequence) that is distinguishable from endogenous nucleic acids or proteins found in natural systems. DNA sequences can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a nucleotide sequence(s) of interest, or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell. As used herein, a "promoter sequence" or "promoter" is a DNA regulatory region capable of binding/recruiting RNA polymerase (e.g., via a transcription initiation complex) and initiating transcription of a downstream (3' direction) sequence (e.g., a protein coding ("coding") or non protein-coding ("non-coding") sequence. A promoter can be any convenient promoter (e.g., a T7 promoter). In some cases, a promoter is a constitutively active promoter (e.g., a promoter that is constitutively in an active/"ON" state), it may be an inducible promoter (e.g., a promoter whose state, active/"ON" or inactive/"OFF", is controlled by an external stimulus, e.g., the presence of a particular temperature, compound, or protein), it may be a spatially restricted promoter (e.g., tissue specific promoter, cell type specific promoter, etc.), and/or it may be a temporally restricted promoter (e.g., the promoter is in the "ON" state or "OFF" state during specific stages of embryonic development or during specific stages of a biological process, e.g., hair follicle cycle in mice).

The terms "DNA regulatory sequences," "control elements," and "regulatory elements," used interchangeably herein, refer to transcriptional (e.g., transcription control elements) and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

"Operably linked" refers to a juxtaposition wherein the components so described are in a relationship permitting them to function in their intended manner. For instance, a promoter is operably linked to a nucleotide sequence (e.g., a protein coding sequence, e.g., a sequence encoding an mRNA; a non protein coding sequence, e.g., a sequence encoding a non-coding RNA (ncRNA) such as a Cas9 guide RNA, a targeter RNA, an activator RNA; and the like) if the promoter affects its transcription and/or expression. The relationship can also be referred to in the reverse and retain the same meaning. For example, a nucleotide sequence of interest can be said to be operably linked to a promoter. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo, ex vivo, or in vitro eukaryotic cell (e.g., a mammalian cell, such as a human cell), a eukaryotic cell present in a multicellular organism, or a cell of a multicellular organism (e.g., a cell line) cultured as a unicellular entity, which eukaryotic cells can be, or have been, used as recipients for a nucleic acid (e.g., an expression vector that comprises a nucleotide sequence of interest), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). CLUSTAL, MUSCLE, and T-COFFEE are additional examples of alignment programs.

"Binding" as used herein (e.g. with reference to binding between an RNA and a protein, e.g., via an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions can generally be characterized by a dissociation constant (Kd), e.g., of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homodimers, homotrimers, etc.) and/or it can bind to one or more molecules of a different protein or proteins.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like. A suitable method of delivering a nucleic acid is via RNP-mediated genetic modification.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In some embodiments, a complex comprising a CRISPR/Cas protein (e.g., a Cas9 protein) and a corresponding guide RNA is used for targeted cleavage of a double stranded DNA (dsDNA), e.g., induction of a double-stranded DNA break (DSB).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.). A "genome editing endonuclease" is an endonuclease that can be used for the editing of a cell's genome (e.g., by cleaving at a targeted location within the cell's genomic DNA). Examples of genome editing endonucleases include but are not limited to, CRISPR/Cas endonucleases (which can in some cases cleave both strands of a target double stranded DNA (dsDNA), and in some cases are nickases, which cleave only one strand of a target dsDNA). Examples of CRISPR/Cas endonucleases include class 2 CRISPR/Cas endonucleases such as: (a) type II CRISPR/Cas proteins, e.g., a Cas9 protein; (b) type V CRISPR/Cas proteins, e.g., a Cpf1 polypeptide, a C2c1 polypeptide, a C2c3 polypeptide, and the like; and (c) type VI CRISPR/Cas proteins, e.g., a C2c2 polypeptide.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

A "host cell" or "target cell" as used herein, denotes an in vivo or in vitro mammalian cell that can be, or have been, used as recipients for a genome targeting composition (e.g., a system of the present disclosure), and include the progeny of the original cell (e.g., when the cell has been transformed by the nucleic acid, or when the cells genome has been modified by the genome targeting composition). It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a subject genome targeting composition (e.g., a system of the present disclosure), e.g., which can include a nucleic acid, e.g., an expression vector. For example, a mammalian host cell can be a genetically modified mammalian host cell (e.g., a mammalian germ cell), by virtue of introduction into a suitable mammalian host cell of an exogenous nucleic acid.

The term "stem cell" is used herein to refer to a cell (e.g., a mammalian stem cell; e.g., a human stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism.

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells. The stem cells may be obtained from any mammalian species, e.g. human, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, e.g., humans, non-human primates, rodents (e.g., rats; mice), and the like.

In some instances, a component (e.g., a nucleic acid component (e.g., a CRISPR/Cas guide RNA); a protein component (e.g., genome editing endonuclease such as a Cas9 protein); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels) (e.g., a fluorescent label) and indirectly detectable labels (indirect labels) (e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label) (e.g., $^3$H, $^{125}$I, $^{35}$S, $^{14}$C, or $^{32}$P); an enzyme (an indirect label) (e.g., peroxidase, alkaline phosphatase, galactosidase, luciferase, glucose oxidase, and the like); a fluorescent protein (a direct label) (e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides genetically modified cells, genetically modified non-human organisms, and methods of producing such cells and organisms. Also provided are methods of editing the genome of such cells and organisms. The genetically modified cells and non-human organisms of the disclosure are genetically modified such that their genome includes an integrated heterologous nucleic acid (that includes a CRISPR/Cas target sequence) at one or more positions within the genome. In some cases, the same CRISPR/Cas target sequence is integrated into 2 or more positions within the genome (e.g., flanking a gene or integrated within two different genes). In some cases, the same CRISPR/Cas target sequence is integrated into 3 or more (e.g., 4 or more, 5 or more, 6 or more, etc.) positions within the genome. The integrated nucleic acids, which include the same CRISPR/Cas target sequence, allow for simultaneous gene editing at multiple different positions within a genome using a single species of CRISPR/Cas guide RNA (i.e., one guide RNA will target multiple sites because the multiple sites have the same target sequence).

In some cases, the CRISPR/Cas target sequence is heterologous to the genome because the sequence is present nowhere in the genome except for where the nucleic acid has integrated. In some cases, the CRISPR/Cas target sequence is heterologous in the sense that it is found elsewhere in the genome, but is not normally present at the position the nucleic acid has integrated.

Cells

A CRISPR/Cas protein (also referred to herein as a CRISPR/Cas endonuclease) interacts with (binds to) a corresponding guide RNA to form a ribonucleoprotein (RNP) complex (referred to herein as a CRISPR/Cas complex) that is targeted to a particular site (a target sequence) in a target genome via base pairing between the guide RNA and a target sequence within the target genome. A guide RNA includes (i) a nucleotide sequence (a guide sequence) that is complementary to a sequence (the target site) of a target DNA and (ii) a protein-binding region that includes a double stranded RNA (dsRNA) duplex and bind to a corresponding CRISPR/Cas protein. The guide RNA can be readily modified in order to target any desired sequence within a target genome (by modifying the guide sequence). A wild type CRISPR/Cas protein (e.g., a Cas9 protein) normally has nuclease activity that cleaves a target nucleic acid (e.g., a double stranded DNA (dsDNA)) at a target site defined by the region of complementarity between the guide sequence of the guide RNA and the target nucleic acid. The term "CRISPR/Cas protein," as used herein, includes wild type CRISPR/Cas proteins, and also variant CRISPR/Cas proteins, e.g., CRISPR/Cas proteins with one or more mutations in a catalytic domain rendering the protein a nickase.

To generate a genetically modified cell of the present disclosure, a heterologous nucleic acid is integrated into the genome of a cell (e.g., any prokaryotic or eukaryotic cell). A heterologous nucleic acid can be any desired length. In some cases, the heterologous nucleic acid has a length in a range of from 17 to 40 nucleotides (nt) (e.g., 17 to 30, 17 to 25, 17 to 22, 17 to 20, 18 to 40, 18 to 30, 18 to 25, 18 to 22, 18 to 20, 19 to 40, 19 to 30, 19 to 25, 19 to 22, 19 to 20, 20 to 40, 20 to 35, 20 to 30, or 20 to 25 nt). In some cases, the heterologous nucleic acid is 17 to 25 nucleotides in length. In some cases, the heterologous nucleic acid is 17 nt in length. In some cases, the heterologous nucleic acid is 18 nt in length. In some cases, the heterologous nucleic acid is 19 nt in length. In some cases, the heterologous nucleic acid is 20 nt in length. In some cases, the heterologous nucleic acid is 18 nt in length. In some cases, the heterologous nucleic acid is 23 nt in length. As noted above, the term "heterologous" is a relative term. In some cases, the heterologous nucleic acid is heterologous to the genome because the sequence is present nowhere in the genome except for where the nucleic acid has integrated. In some cases, the heterologous nucleic acid is heterologous in the sense that it is found elsewhere in the genome, but is not normally present at the position the nucleic acid has integrated (i.e., it is heterologous to the position at which it is integrated) (i.e., the sequence is not present at that position in the genome in the parent cell that was used to produce the genetically modified cell.

Many methods for integrated foreign nucleic acids into the genomes of various cell types will be known to one of ordinary skill in the art and any convenient method can be used (e.g., a CRISPR/Cas system can be used to generate the genetically modified cells and organisms described herein). A nucleic acid that is integrated into the genome at one or more positions includes a CRISPR/Cas target sequence. In some cases, two or more nucleic acids (having the same CRISPR/Cas target sequence) (3 or more, 4 or more, 5 or more, 6 or more, etc.) are integrated into two or more different positions within the same locus (e.g., flanking a nucleotide sequence encoding a protein and/or an RNA, or a transcription control element). In some cases, two or more (3 or more, 4 or more, 5 or more, 6 or more, etc.) nucleic acids (having the same CRISPR/Cas target sequence) are integrated into two or more different loci (e.g., into nucleotide sequences that encode two different proteins). In some cases, at least two of the two or more positions are within 1 kilobase (1 kb) of one another.

The term "locus" as used herein refers to a position (which position can be particular base pair location, or can be a range of from one base pair to another) within a genome of interest. For example, a locus can be a particular base pair position (as an illustrative example—base pair 10,324 of human chromosome 14 would be a particular base pair position). As another example, a locus can be a range of base pair positions, e.g., the position in the genome that codes a particular protein or RNA that is transcribed (as an illustrative example, the Wnt3A locus is a protein-coding locus that is transcribed and encodes the Wnt3A protein). As used herein, the term protein-coding locus or RNA-coding locus generally includes the transcriptional control sequences that influence transcription of the locus. Thus, for example, the term "protein-coding locus" not only refers to the nucleotide sequences that have an open reading frame (ORF) and directly encode the protein, but also the promoter, the 5' UTR, the 3' UTR, etc. Thus, when a heterologous nucleic acid is integrated into a protein-coding locus, it will be understood that the purpose is to integrate a CRISPR/Cas target sequence for later recognition by a CRISPR/Cas complex, and that editing a promoter of a protein-coding sequence can in some cases accomplish the same goal as editing the protein-coding sequence itself (e.g., when the goal is to cleave at the CRISPR/Cas target sequence in order to reduce expression of the protein encoding by the locus).

A target DNA (e.g., genomic DNA) that can be recognized and cleaved by a CRISP/Cas protein (e.g., Cas9) is a DNA polynucleotide that comprises a "target site" or "target sequence." The terms "CRISPR/Cas target site" or "CRISPR/Cas target sequence" are used interchangeably herein to refer to a nucleic acid sequence present in a target DNA (e.g., genomic DNA of a cell) to which a CRISPR/Cas guide RNA can bind, allowing cleave of the target DNA by the CRISPR/Cas endonuclease. The strand of the target DNA that is complementary to and hybridizes with the CRISPR/Cas guide RNA is referred to as the "complementary strand" or the "target strand' and the strand of the target DNA that is complementary to the "complementary strand" (and is therefore not complementary to the guide RNA) is referred to as the "non-complementary strand" or "non-target strand." A target sequence can be any desired length and in some cases can depend upon the type of CRISPR/Cas guide RNA and CRISPR/Cas protein that will be used to target the target sequence. In some cases, the CRISPR/Cas target sequence has a length in a range of from 17 to 40 nucleotides (nt) (e.g., 17 to 30, 17 to 25, 17 to 22, 17 to 20, 18 to 40, 18 to 30, 18 to 25, 18 to 22, 18 to 20, 19 to 40, 19 to 30, 19 to 25, 19 to 22, 19 to 20, 20 to 40, 20 to 35, 20 to 30, or 20 to 25 nt). In some cases, the CRISPR/Cas target sequence is 17 to 25 nucleotides in length. In some cases, the CRISPR/Cas target sequence is 17 nt in length. In some cases, the CRISPR/Cas target sequence is 18 nt in length. In some cases, the CRISPR/Cas target sequence is 19 nt in length. In some cases, the CRISPR/Cas target sequence is 20 nt in length.

A feature that renders the target sequence functional (such that it can be recognized and cleaved by a CRISPR/Cas complex) is that it is adjacent to a protospacer adjacent motif (PAM), also referred to as a "PAM sequence." Once a nucleic acid is integrated into the genome (when generating a subject genetically modified cell/organism), the CRISPR/Cas target sequence is adjacent to a PAM. The PAM can be present at that position in the genome prior to the integration (e.g., the nucleic acid can be integrated such that the CRISPR/Cas target sequence is inserted next to the PAM that was already present in the genome. In some cases, the PAM is not present at the desired position in the genome, and the PAM is instead present on the nucleic acid to be integrated. Such a heterologous nucleic acid would therefore include the CRISPR/Cas target sequence adjacent to a PAM sequence, and both the CRISPR/Cas target sequence and the PAM would be integrated into the genome.

"Protospacer Adjacent Motif" (PAM)

As noted above, a wild type CRISPR/Cas protein (e.g., Cas9 protein) normally has nuclease activity that cleaves a target nucleic acid (e.g., a double stranded DNA (dsDNA)) at a target site defined by the region of complementarity between the guide sequence of the guide RNA and the target nucleic acid. In some cases, site-specific targeting to the target nucleic acid occurs at locations determined by both (i) base-pairing complementarity between the guide nucleic acid and the target nucleic acid; and (ii) a short motif referred to as the "protospacer adjacent motif" (PAM) in the target nucleic acid. For example, when a Cas9 protein binds to (in some cases cleaves) a dsDNA target nucleic acid, the PAM sequence that is recognized (bound) by the Cas9 polypeptide is present on the non-complementary strand (the strand that does not hybridize with the targeting segment of the guide nucleic acid) of the target DNA. In some cases, a PAM sequence has a length in a range of from 1 nt to 15 nt (e.g., 1 nt to 14 nt, 1 nt to 13 nt, 1 nt to 12 nt, 1 nt to 11 nt, 1 nt to 10 nt, 1 nt to 9 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 2 nt to 3 nt, 2 nt, or 3 nt).

CRISRPR/Cas (e.g., Cas9) proteins from different species can have different PAM sequence requirements. For example, in some embodiments (e.g., when the Cas9 protein is derived from *S. pyogenes* or a closely related Cas9 is used; see for example, Chylinski et al., RNA Biol. 2013 May; 10(5):726-37; and Jinek et al., Science. 2012 Aug. 17; 337(6096):816-21; both of which are hereby incorporated by reference in their entirety), the PAM sequence is NRG because the *S. pyogenes* Cas9 PAM (PAM sequence) is NAG or NGG (or NRG where "R" is A or G). For example, a Cas9 PAM sequence for *S. pyogenes* Cas9 is: NGG, NAG, AGG, CGG, GGG, TGG, AAG, CAG, GAG, and TAG.

In some embodiments (e.g., when a Cas9 protein is derived from the Cas9 protein of *Neisseria meningitidis* or a closely related Cas9 is used), the PAM sequence (e.g., of a target nucleic acid) can be 5'-NNNNGANN-3', 5'-NNNNGTTN-3', 5'-NNNNGNNT-3', 5'-NNNNGTNN-3', 5'-NNNNGNTN-3', or 5'-NNNNGATT-3', where N is any nucleotide. In some embodiments (e.g., when a Cas9 protein is derived from *Streptococcus thermophilus* #1 or a closely related Cas9 is used), the PAM sequence (e.g., of a target nucleic acid) can be 5'-NNAGAA-3', 5'-NNAGGA-3', 5'-NNGGAA-3', 5'-NNANAA-3', or 5'-NNGGGA-3' where N is any nucleotide. In some embodiments (e.g., when a Cas9 protein is derived from *Treponema denticola* (TD) or a closely related Cas9 is used), the PAM sequence (e.g., of a target nucleic acid) can be 5'-NAAAAN-3', 5'-NAAAAC-3', 5'-NAAANC-3', 5'-NANAAC-3', or 5'-NNAAAC-3', where N is any nucleotide. As would be known by one of ordinary skill in the art, additional PAM sequences for other Cas9 polypeptides can readily be determined using bioinformatic analysis (e.g., analysis of genomic sequencing data). See Esvelt et al., Nat Methods. 2013 November; 10(11):1116-21, for additional information.

Target Cells, Genetically Modified Cells, and Non-Human Genetically Modified Organisms Because the CRISPR/Cas guide RNA provides specificity by hybridizing to target DNA, any cell of interest can be a target cell for use with a CRISPR/Cas complex; thus, any type of cell is suitable to be a subject genetically modified cell. For example, a subject genetically modified cell can be a mitotic or post-mitotic cell, and can be a cell of any organism (e.g. a prokaryotic cell, a bacterial cell, an archaeal cell, a cell of a single-cell eukaryotic organism, a plant cell, an algal cell (e.g., *Botryococcus braunii, Chlamydomonas reinhardtii, Nannochloropsis gaditana, Chlorella pyrenoidosa, Sargassum patens, C. agardh*, and the like), a fungal cell (e.g., a yeast cell), an animal cell, a cell of an invertebrate animal (e.g. fruit fly, cnidarian, echinoderm, nematode, mosquito, etc.), a cell of a vertebrate animal (e.g., fish, amphibian, reptile, bird, mammal), a cell of a mammal (e.g., a pig, a cow, a goat, a sheep, a rodent, a rat, a mouse, a non-human primate, a human), a cell of a rodent (e.g., mouse, rat), a cell of a non-human primate, a cell of a human, etc.). The cells can be in vitro (e.g., in culture), ex vivo (e.g., primary cells from an individual), or in vivo (e.g., can be a cell of a cell a non-human transgenic organism).

Any cell type can also be suitable (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture.

Because a subject genetically modified cell can be a cell of any organism, a subject non-human genetically modified organism can be any type of organism (with the exception of human). Suitable organisms for the include but are not limited to prokaryotes, bacteria, archaea, single-cell eukaryotic organisms, plants (dicot, monoct, agricultural crop plan, tomato plant, rice, corn, wheat, soy, potato, etc.), algae (e.g., *Botryococcus braunii, Chlamydomonas reinhardtii, Nannochloropsis gaditana, Chlorella pyrenoidosa, Sargassum patens C. Agardh*, and the like), fungi (e.g., yeast), animals, invertebrates (e.g. fruit fly, cnidarian, echinoderm, nematode, mosquito, etc.), vertebrates (e.g., fish, amphibian, reptile, bird, mammal), mammals (e.g., pig, cow, goat, sheep, rodent, rat, mouse, dog, cat, non-human primate), and the like.

CRISPR/Cas Endonucleases

Examples of suitable RNA-guided endonucleases include, but are not limited to, CRISPR/Cas endonucleases (e.g., class 2 CRISPR/Cas endonucleases such as a type II, type V, or type VI CRISPR/Cas endonucleases). In some cases, a suitable RNA-guided endonuclease is a class 2 CRISPR/Cas endonuclease. In some cases, a suitable RNA-guided endonuclease is a class 2 type II CRISPR/Cas endonuclease (e.g., a Cas9 protein). In some cases, a suitable RNA-guided endonuclease is a class 2 type V CRISPR/Cas endonuclease (e.g., a Cpf1 protein, a C2c1 protein, or a C2c3 protein). In some cases, a suitable RNA-guided endonuclease is a class 2 type VI CRISPR/Cas endonuclease (e.g., a C2c2 protein).

In some cases, an RNA-guided endonuclease is a fusion protein that is fused to a heterologous polypeptide (also referred to as a "fusion partner"). In some cases, an RNA-guided endonuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.). In some embodiments, an RNA-guided endonuclease is fused to an amino acid sequence (a fusion partner) that provides a tag (i.e., the fusion partner is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some cases, the fusion partner can provide for increased or decreased stability (i.e., the fusion partner can be a stability control peptide, e.g., a degron, which in some cases is controllable (e.g., a temperature sensitive or drug controllable degron sequence).

In some cases, an RNA-guided endonuclease is conjugated (e.g., fused) to a polypeptide permeant domain to promote uptake by the cell (i.e., the fusion partner promotes uptake by a cell). A number of permeant domains are known in the art and may be used, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 1080). As another example, the permeant peptide can comprise the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site can be determined by routine experimentation.

In some cases, a genome editing nuclease includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., a genome editing nuclease, e.g., a Cas9 protein). In some embodiments, a PTD is covalently linked to the carboxyl terminus of a polypeptide (e.g., an RNA-guided endonuclease, e.g., a Cas9 protein). In some cases, the PTD is inserted internally in the RNA-guided endonuclease (e.g., Cas9 protein) (i.e., is not at the N- or C-terminus of the genome editing nuclease). In some cases, an RNA-guided endonuclease (e.g., a Cas9 protein) includes (is conjugated to, is fused to) one or more PTDs (e.g., two or more, three or more, four or more PTDs). In some cases a PTD includes a nuclear localization signal (NLS) (e.g., in some cases 2 or more, 3 or more, 4 or more, or 5 or more NLSs).

In some cases, an RNA-guided endonuclease (e.g., a Cas9 protein) includes one or more NLSs (e.g., 2 or more, 3 or more, 4 or more, or 5 or more NLSs). In some embodiments, a PTD is covalently linked to a nucleic acid (e.g., a CRISPR/Cas guide RNA, a polynucleotide encoding a CRISPR/Cas guide RNA, a polynucleotide encoding a class 2 CRISPR/Cas endonuclease such as a Cas9 protein or a type V or type VI CRISPR/Cas protein, etc.). Examples of PTDs include but are not limited to a minimal undecapeptide protein transduction domain (corresponding to residues 47-57 of HIV-1 TAT comprising YGRKKRRQRRR; SEQ ID NO: 1076); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:1077); Transportan GWTLNSAGYLLG-KINLKALAALAKKIL (SEQ ID NO:1078); KALAWEAKLAKALAKALAKHLAKALAKALKCEA (SEQ ID NO:1079); and RQIKIWFQNRRMKWKK (SEQ ID NO: 1080). Exemplary PTDs include but are not limited to, YGRKKRRQRRR (SEQ ID NO:1081), RKKRRQRRR (SEQ ID NO:1082); an arginine homopolymer of from 3 arginine residues to 50 arginine residues; Exemplary PTD domain amino acid sequences include, but are not limited to, any of the following: YGRKKRRQRRR (SEQ ID NO:1083); RKKRRQRR (SEQ ID NO:1084); YARAAAR-QARA (SEQ ID NO:1085); THRLPRRRRRR (SEQ ID NO:1086); and GGRRARRRRRR (SEQ ID NO:1087). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching poly-anion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

An RNA-guided endonuclease (e.g., a Cas9 protein) can have multiple (1 or more, 2 or more, 3 or more, etc.) fusion partners in any combination of the above. As an illustrative example, an RNA-guided endonuclease (e.g., a Cas9 protein) can have a fusion partner that provides for tagging (e.g., GFP), and can also have a subcellular localization sequence (e.g., one or more NLSs). In some cases, such a fusion protein might also have a tag for ease of tracking and/or purification (e.g., a histidine tag, e.g., a 6×His tag; a hemagglutinin (HA) tag; a FLAG tag; a Myc tag; and the like). As another illustrative example, an RNA-guided endonuclease (e.g., a Cas9 protein) can have one or more NLSs (e.g., two or more, three or more, four or more, five or more, 1, 2, 3, 4, or 5 NLSs). In some cases a fusion partner (or multiple fusion partners, e.g., 1, 2, 3, 4, or 5 NLSs) (e.g., an NLS, a tag, a fusion partner providing an activity, etc.) is located at or near the C-terminus of the RNA-guided endonuclease (e.g., Cas9 protein). In some cases a fusion partner (or multiple fusion partners, e.g., 1, 2, 3, 4, or 5 NLSs) (e.g., an NLS, a tag, a fusion partner providing an activity, etc.) is located at the N-terminus of the RNA-guided endonuclease (e.g., Cas9 protein). In some cases the genome editing nuclease (e.g., Cas9 protein) has a fusion partner (or multiple fusion partners, e.g., 1, 2, 3, 4, or 5 NLSs) (e.g., an NLS, a tag, a fusion partner providing an activity, etc.) at both the N-terminus and C-terminus.

Class 2 CRISPR/Cas Endonucleases

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In some embodiments, an RNA-guided endonuclease nuclease of a system of the present disclosure is a class 2 CRISPR/Cas endonuclease. Thus in some cases, a system of the present disclosure includes a class 2 CRISPR/Cas endonuclease (or a nucleic encoding the endonuclease). In class 2 CRISPR systems, the functions of the effector complex (e.g., the cleavage of target DNA) are carried out by a single endonuclease (e.g., see Zetsche et al, Cell. 2015 Oct. 22; 163(3): 759-71; Makarova et al, Nat Rev Microbiol. 2015 November; 13(11):722-36; and Shmakov et al., Mol Cell. 2015 Nov. 5; 60(3):385-97). As such, the term "class 2 CRISPR/Cas protein" is used herein to encompass the endonuclease (the target nucleic acid cleaving protein) from class 2 CRISPR systems. Thus, the term "class 2 CRISPR/Cas endonuclease" as used herein encompasses type II CRISPR/Cas proteins (e.g., Cas9), type V CRISPR/Cas proteins (e.g., Cpf1, C2c1, C2C3), and type VI CRISPR/Cas proteins (e.g., C2c2). To date, class 2 CRISPR/Cas proteins encompass type II, type V, and type VI CRISPR/Cas proteins, but the term is also meant to encompass any class 2 CRISPR/Cas protein suitable for binding to a corresponding guide RNA and forming an RNP complex.

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a single-guide RNA (sgRNA), Cas9 generates site-specific DSBs or SSBs (for example, when one of the catalytic domains harbors an inactivating mutation) within double-stranded DNA (dsDNA) target nucleic acids, which are repaired either by non-homologous end joining (NHEJ) or homology-directed recombination (HDR).

As noted above, in some cases, a system of the present disclosure includes a type II CRISPR/Cas endonuclease. A type II CRISPR/Cas endonuclease is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail) (e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to *Streptococcus pyogenes* Cas9).

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a chimeric Cas9 protein includes a heterologous polypeptide that has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a chimeric Cas9 protein includes a heterologous polypeptide that has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 does present motifs that can be used to help determine whether a given protein is a Cas9 protein.

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 95% or more amino acid sequence identity to motifs 1-4 of

TABLE 1

Table 1 lists 4 motifs that are present in Cas9 sequences from various species. The amino acids listed in Table 1 are from the Cas9 from *S. pyogenes* (SEQ ID NO: 5).

| Motif # | Motif | Amino acids (residue #s) | Highly conserved |
| --- | --- | --- | --- |
| 1 | RuvC-like I | IGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDKN (837-863) (SEQ ID NO: 3) | H840, N854, N863 |
| 4 | RuvC-like III | HHAHDAYL (982-989) (SEQ ID NO: 4) | H982, H983, A984, D986, A987 | the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs: 1-4), or to the corresponding portions in any of the amino acid sequences set forth as SEQ ID NOs: 6-816.

In some cases, a suitable Cas9 polypeptide is a high fidelity (HF) Cas9 polypeptide (e.g., see Kleinstiver et al. (2016) *Nature* 529:490). For example, amino acids N497, R661, Q695, and Q926 of the amino acid sequence set forth as (SEQ ID NO:5) (or the corresponding position of another Cas9 protein, e.g., a protein having the amino acid sequence of any of the sequences set forth as SEQ ID NOs: 6-816) are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence set forth as SEQ ID NO:5 where amino acids N497, R661, Q695, and Q926 are substituted, e.g., with alanine. For example, in some cases, an HF Cas9 polypeptide comprises the amino acid sequence set forth as SEQ ID NO:1138.

In some cases, a suitable Cas9 polypeptide exhibits altered PAM specificity. See, e.g., Kleinstiver et al. (2015) *Nature* 523:481.

As used herein, the term "Cas9 protein" encompasses a "chimeric Cas9 protein." As used herein, the term "Cas9 protein" encompasses a variant Cas9 that is a nickase.

Variant Cas9 Proteins—Nickases

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816.

Type V and Type VI CRISPR/Cas Endonucleases

In some cases, a system of the present disclosure includes a type V or type VI CRISPR/Cas endonuclease (i.e., the genome editing endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas endonuclease is C2c2. In some cases, a system of the present disclosure includes a type V CRISPR/Cas endonuclease (e.g., Cpf1, C2c1, C2c3). In some cases, a Type V CRISPR/Cas endonuclease is a Cpf1 protein. In some cases, a system of the present disclosure includes a type VI CRISPR/Cas endonuclease (e.g., C2c2).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs: 1088-1092.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 1088-1092.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 1088-1092), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., a D→A substitution) at an amino acid residue corresponding to amino acid 917 of the Cpf1 amino acid sequence set forth in SEQ ID NO: 1088. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., an E→A substitution) at an amino acid residue corresponding to amino acid 1006 of the Cpf1 amino acid sequence set forth in SEQ ID NO: 1088. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., a D→A substitution) at an amino acid residue corresponding to amino acid 1255 of the Cpf1 amino acid sequence set forth in SEQ ID NO: 1088.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092.

In some cases a type V CRISPR/Cas endonuclease is a C2c1 protein (examples include those set forth as SEQ ID NOs: 1112-1119). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 1112-1119.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 1112-1119). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 1112-1119.

In some cases, the C2c1 protein exhibits reduced enzymatic activity relative to a wild-type C2c1 protein (e.g., relative to a C2c1 protein comprising the amino acid sequence set forth in any of SEQ ID NOs: 1112-1119), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 1112-1119.

In some cases a type V CRISPR/Cas endonuclease is a C2c3 protein (examples include those set forth as SEQ ID NOs: 1120-1123). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 1120-1123.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 1120-1123.

In some cases, the C2c3 protein exhibits reduced enzymatic activity relative to a wild-type C2c3 protein (e.g., relative to a C2c3 protein comprising the amino acid sequence set forth in any of SEQ ID NOs: 1120-1123), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 1120-1123.

In some cases a type VI CRISPR/Cas endonuclease is a C2c2 protein (examples include those set forth as SEQ ID NOs: 1124-1135). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 1124-1135.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 1124-1135.

In some cases, the C2c2 protein exhibits reduced enzymatic activity relative to a wild-type C2c2 protein (e.g., relative to a C2c2 protein comprising the amino acid sequence set forth in any of SEQ ID NOs: 1124-1135), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 1124-1135.

Guide RNA (for CRISPR/Cas Endonucleases)

A nucleic acid that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA."

A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules: an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Cas9 Guide RNA

A nucleic acid molecule that binds to a Cas9 protein and targets the complex to a specific location within a target nucleic acid is referred to herein as a "Cas9 guide RNA."

A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence can be taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above) (in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075, or complements thereof. For example, in some cases, sequences from SEQ ID NOs: 827-957 (which are from tracrRNAs) or complements thereof, can pair with sequences from SEQ ID NOs: 964-1075 (which are from crRNAs), or complements thereof, to form a dsRNA duplex of a protein binding segment.

Targeting Segment of a Cas9 Guide RNA

The first segment of a subject guide nucleic acid includes a guide sequence (i.e., a targeting sequence) (a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Protein-Binding Segment of a Cas9 Guide RNA

The protein-binding segment of a subject Cas9 guide RNA interacts with a Cas9 protein. The Cas9 guide RNA guides the bound Cas9 protein to a specific nucleotide sequence within target nucleic acid via the above mentioned targeting segment. The protein-binding segment of a Cas9 guide RNA comprises two stretches of nucleotides that are complementary to one another and hybridize to form a double stranded RNA duplex (dsRNA duplex). Thus, the protein-binding segment includes a dsRNA duplex. In some cases, the protein-binding segment also includes stem loop 1 (the "nexus") of a Cas9 guide RNA. For example, in some cases, the activator of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "nexus"). For example, in some cases, the protein-binding segment includes stem loop 1 (the "nexus") of a Cas9 guide RNA. In some cases, the protein-binding segment includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., S. pyogenes guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "nexus"); the next stem loop is called "stem loop 2" (and is also referred to herein as the "hairpin 1"); and the next stem loop is called "stem loop 3" (and is also referred to herein as the "hairpin 2").

In some cases, a Cas9 guide RNA (sgRNA or dgRNA) (e.g., a full length Cas9 guide RNA) has stem loops 1, 2, and 3. In some cases, an activator (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loops 1, 2, and 3.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences. Although a number of different alternative sequences can be used, an example Cas9 single guide RNA (based on crRNA and tracrRNA from *S. pyogenes*, where the dsRNA duplex of the protein-binding segment is truncated relative to the dsRNA duplex present in the wild type dual guide RNA) can include the sequence set forth in SEQ ID NO: 958 (This example sequence does not include the guide sequence. The guide sequence, which varies depending on the target, would be 5' of this example sequence. The activator in this example is 66 nucleotides long).

Examples of various Cas9 proteins and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife 2013; 2:e00471; Pattanayak et al., Nat Biotechnol. 2013 September; 31(9):839-43; Qi et al., Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Guide RNAs Corresponding to Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

A type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt,).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex).

The target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

The guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

The guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

The duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an example, a duplex-forming segment of a Cpf1 guide RNA can comprise a nucleotide sequence selected from (5' to 3'): AAUUUCUACUGUUGUAGAU (SEQ ID NO: 1093), AAUUUCUGCUGUUGCAGAU (SEQ ID NO: 1094), AAUUUCCACUGUUGUGGAU (SEQ ID NO: 1095), AAUUCCUACUGUUGUAGGU (SEQ ID NO: 1096), AAUUUCUACUAUUGUAGAU (SEQ ID NO: 1097), AAUUUCUACUGCUGUAGAU (SEQ ID NO: 1098), AAUUUCUACUUUGUAGAU (SEQ ID NO: 1099), and AAUUUCUACUUUGUAGAU (SEQ ID NO: 1100). The guide sequence can then follow (5' to 3') the duplex forming segment.

A non-limiting example of an activator RNA (e.g. tracrRNA) of a C2c1 guide RNA (dual guide or single guide) is an RNA that includes the nucleotide sequence GAAUUUUUCAACGGGUGUGCCAAUGGCCAC-UUUCCAGGUGGCAAAGCCCGUUGA GCUUCU-CAAAAAG (SEQ ID NO: 1101). In some cases, a C2c1 guide RNA (dual guide or single guide) is an RNA that includes the nucleotide sequence In some cases, a C2c1 guide RNA (dual guide or single guide) is an RNA that includes the nucleotide sequence GUCUA-GAGGACAGAAUUUUUCAACGGGUGUGC-CAAUGGCCACUUUCCAGGUGGC AAAGCCCGUUGAGCUUCUCAAAAAG (SEQ ID NO: 1102). In some cases, a C2c1 guide RNA (dual guide or single guide) is an RNA that includes the nucleotide sequence UCUAGAGGACAGAAUUUUUCAACGGGU-GUGCCAAUGGCCACUUUCCAGGUGGCA AAGCCCGUUGAGCUUCUCAAAAAG (SEQ ID NO: 1103). A non-limiting example of an activator RNA (e.g. tracrRNA) of a C2c1 guide RNA (dual guide or single guide) is an RNA that includes the nucleotide sequence ACUUUCCAGGCAAAGCCCGUUGAGCUUCU-CAAAAAG (SEQ ID NO: 1104). In some cases, a duplex forming segment of a C2c1 guide RNA (dual guide or single guide) of an activator RNA (e.g. tracrRNA) includes the nucleotide sequence AGCUUCUCA (SEQ ID NO: 1105) or the nucleotide sequence GCUUCUCA (SEQ ID NO: 1106) (the duplex forming segment from a naturally existing tracrRNA.

A non-limiting example of a targeter RNA (e.g. crRNA) of a C2c1 guide RNA (dual guide or single guide) is an RNA with the nucleotide sequence CUGAGAAGUGGCACNNNNNNNNNNNNNNNNNNNN (SEQ ID NO: 1107), where the Ns represent the guide sequence, which will vary depending on the target sequence, and although 20 Ns are depicted a range of different lengths are acceptable. In some cases, a duplex forming segment of a C2c1 guide RNA (dual guide or single guide) of a targeter RNA (e.g. crRNA) includes the nucleotide sequence CUGAGAAGUGGCAC (SEQ ID NO: 1108) or includes the nucleotide sequence CUGAGAAGU (SEQ ID NO: 1109) or includes the nucleotide sequence UGAGAAGUGGCAC (SEQ ID NO: 1110) or includes the nucleotide sequence UGAGAAGU (SEQ ID NO: 1111).

Examples and guidance related to type V or type VI CRISPR/Cas endonucleases and guide RNAs (as well as information regarding requirements related to protospacer adjacent motif (PAM) sequences present in targeted nucleic acids) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

In some cases, the genetically modified organism will include a nucleic acid encoding a CRISPR/Cas endonuclease (e.g., a Cas9 protein). In such cases, the nucleotide sequence encoding the CRISPR/Cas endonuclease and/or a transcription control element that is operably linked to the nucleotide sequence will include a CRISPR/Cas target sequence (e.g., via a subject heterologous integrated nucleic acid). In some cases that CRISPR/Cas target sequence will be the same as the CRISPR/Cas target sequence integrated elsewhere in the genome. In some cases that CRISPR/Cas target sequence will be different than the target sequence integrated elsewhere (e.g., will be a second CRISPR/Cas target sequence), and a second guide RNA (a second species of guide RNA, having a guide sequence that hybridizes with the second target sequence) would be needed to target the second target sequence. In some cases, the nucleic acid encoding the CRISPR/Cas endonuclease (e.g., a Cas9 protein) will be integrated into the genome of the genomically modified cell/organism and in some cases, the nucleic acid will not be integrated (e.g., will be episomally or transiently maintained).

Provided are methods of editing the genome or modulating transcription of a subject genetically modified cell (or non-human organism). The components of a CRISPR/Cas system can be delivered (introduced into a cell) as DNA, RNA, or protein. For example, when the composition includes a class 2 CRISPR/Cas endonuclease (e.g., Cas9, Cpf1, etc.) and a corresponding guide RNA (e.g., a Cas9 guide RNA, a Cpf1 guide RNA, etc.), the endonuclease and guide RNA can be delivered (introduced into the cell) as an RNP complex (i.e., a pre-assembled complex of the CRISPR/Cas endonuclease and the corresponding CRISPR/Cas guide RNA). Thus, a class 2 CRISPR/Cas endonuclease can be introduced into a cell as a protein. Alternatively, a class 2 CRISPR/Cas endonuclease can be introduced into a cell as a nucleic acid (DNA and/or RNA) encoding the endonuclease. A CRISPR/Cas guide RNA can be introduced into a cell as RNA, or as DNA encoding the guide RNA. In cases where the genetically modified cell includes a nucleic acid encoding the CRISPR/Cas endonuclease, e.g., under the control of an inducible promoter, the method may include inducing expression of the CRISPR/Cas endonuclease.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" it is meant a nucleic acid sequence to be inserted at the site cleaved by the CRISPR/Cas protein. The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

Utilities

The compositions and methods described herein provide an approach to utilizing CRIPSR/Cas technology for a more precise, efficient, and controlled system that is not limited by the restrictions that sometimes hinder approaches using a native target sequence (e.g., using one guide RNA for each desired target locus). The compositions and methods disclosed herein are useful in the generation of cell libraries, synthetic genome construction, and rapid multiplexing that is not limited by guide sequence or position.

As disclosed and demonstrated here, construction of a small number of parental lineages harboring unique Cas9 target sites (present at all desired loci) would allow for the rapid and efficient cloning of strains with either wild-type (WT) alleles, temperature sensitive alleles, deletions, or tagged alleles of any number of genes of interest in a single step with no cloning of any guide RNA cassettes. Moreover, elimination of sequences encoding the CRISPR/Cas protein (e.g., Cas9) itself (e.g., by integrating one or more CRISPR/Cas target sequences into the CRISPR/Cas protein encoding locus) could occur simultaneously, resulting in an otherwise isogenic WT strain.

The methods and compositions (e.g. cells and cell libraries) are useful for those studying multiple genes in a signaling pathway, subunits within a multi-protein macromolecular complex, closely related paralogous gene groups, or any combination of a collection of genes of interest. For example, the same target sequence can be inserted into multiple loci (e.g., for the purpose of later editing the genome and/or altering transcription at those loci). For example, the same CRISPR/Cas target sequence can be integrated such that it flanks or integrates into two or more different protein-coding sequences, RNA-coding sequences, or transcription control elements. In this way, multiple genes (proteins, or RNAs) can be later targeted by a CRISPR/Cas complex using only one guide RNA (one species of guide RNA). In other words, only one guide sequence would be needed to target any locus at which one or more heterologous nucleic acids have been integrated into the genome.

As an example, in cases where multiple paralogs of a gene of interest are present in the genome (e.g., the human genome has multiple Wnt proteins), genetic redundancy can complicate investigations. Using the present disclosed strategy, only one guide RNA would be needed to simultaneously edit the genome at multiple loci and one could even knockout all paralogs at one time. This would allow not only for more clear determination of the consequences of removing gene function, but would also allow for add-back experiments in which, once all paralogs are removed, nucleic acids encoding individual paralogs, or groups of paralogs (e.g., pools), can be 'added back' in order to study their function.

The same principals/strategies can be applied to studying multiple members of a multi-subunit complex, multiple proteins of a signal pathway, and the like.

When not using the system described here, time and effort are often put into testing various guide sequences and slightly different genomic target(s) at a particular locus to determine which position or combination of guide RNAs results in the most efficient level of genomic integration. The method disclosed here could be used to study and interrogate the effects of genomic positioning and local chromatin structure and content since the same CRISPR/Cas target sequence can be artificially placed at varying positions (and is controlled for sequence identity across all loci).

Integrating a heterologous CRISPR/Cas target sequence into the genome of an organism can also be very useful in gene drive strategies. For example, as a fail safe against a 'runaway' type of gene drive or to 'turn off' a gene drive, the same target sequence can be integrated into two or more different target loci (e.g., encoding essential genes) in the gene drive organism such that a CRISPR/Cas complex becomes active (e.g., associates, the guide RNA is expressed, the endonuclease is expressed) only under particular desirable circumstances (e.g., induced by a user, induced by a particular biological input, and the like), and once active, the complex then targets the multiple targets (e.g., essential genes). Placing the same target sequence at multiple loci would aid in preventing 'escape' (e.g., mutation of a target sequence at one locus (e.g., at a single locus) would not allow the gene drive organism to escape the fail safe).

As another example, a heterologous CRISPR/Cas target sequence can flank or be incorporated into a particular gene of interest that plays a role in the mechanism of the gene drive strategy. Thus, when working with (studying) the organism in the lab, when it would be very desirable to reduce the chance that an escaped gene drive organism (e.g., a mosquito) encounters a wild type organism (i.e., it would be desirable to prevent the triggering of a gene drive before it is 'ready' (i.e., before the gene drive is desired). In this way, even if the gene drive organism encounters a wild type organism, the wild type organism would not contain that target sequence in its genome and wild type genomes would not be targeted.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-58 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A genetically modified cell,
wherein the genetically modified cell is genetically modified with a first heterologous nucleic acid that: (i) is integrated into one or more positions within the genetically modified cell's genome, (ii) comprises a first CRISPR/Cas target sequence, and (iii) has a length in a range of from 17 to 40 nucleotides (nt), wherein the first CRISPR/Cas target sequence is adjacent to a protospacer adjacent motif (PAM) at each position the first heterologous nucleic acid is integrated.

2. The genetically modified cell of 1, wherein the genetically modified cell is a eukaryotic cell.

3. The genetically modified cell of 2, wherein the genetically modified cell is a fungal cell, a plant cell, an invertebrate cell, a vertebrate cell, or a mammalian cell.

4. The genetically modified cell of any one of 1-3, wherein said first CRISPR/Cas target sequence is not present in the genome of a parent cell used to make the genetically modified cell.

5. The genetically modified cell of any one of 1-4, wherein the first heterologous nucleic acid comprises the PAM.

6. The genetically modified cell of any one of 1-5, wherein said first heterologous nucleic acid is integrated into a position that is within a protein-coding sequence, an RNA-coding sequence, or a transcription control element.

7. The genetically modified cell of any one of 1-6, wherein said first heterologous nucleic acid is integrated into two or more positions within the genome.

8. The genetically modified cell of 7, wherein at least two of the two or more positions: (i) are within protein-coding sequences, RNA-coding sequences, or transcription control elements; or (ii) flank a protein-coding sequence, an RNA-coding sequence, or a transcription control element.

9. The genetically modified cell of 7 or 8, wherein said first heterologous nucleic acid is integrated into, or flanks, two or more different protein-coding sequences, RNA-coding sequences, or transcription control elements.

10. The genetically modified cell of any one of 7-9, wherein said first heterologous nucleic acid is integrated into at least two positions that are within 1 kilobase (1 kb) of one another.

11. The genetically modified cell of any one of 1-10, wherein the genetically modified cell comprises a CRISPR/Cas endonuclease and/or a nucleic acid comprising a nucleotide sequence encoding the CRISPR/Cas endonuclease.

12. The genetically modified cell of 11, wherein the nucleic acid comprising the nucleotide sequence encoding the CRISPR/Cas endonuclease is a heterologous nucleic acid that is episomally maintained or integrated into the genetically modified cell's genome.

13. The genetically modified cell of 11 or 12, wherein the CRISPR/Cas endonuclease (i) is a chimeric CRISPR/Cas fusion protein and/or (ii) has nickase activity or lacks nuclease activity.

14. The genetically modified cell of any one of 11-13, wherein the CRISPR/Cas endonuclease is selected from: a class 2 CRISPR/Cas endonuclease, a Cas9 protein, a type V CRISPR/Cas endonuclease, a type VI CRISPR/Cas endonuclease, a Cpf1 protein, a C2c1 protein, a C2c3 protein, and a C2c2 protein.

15. The genetically modified cell of 14, wherein the CRISPR/Cas endonuclease is a Cas9 protein.

16. The genetically modified cell of any one of 11-15, wherein the nucleotide sequence encoding the CRISPR/Cas endonuclease is operably linked to a promoter.

17. The genetically modified cell of 16, wherein the promoter is an inducible promoter.

18. The genetically modified cell of any one of 11-17, wherein the genetically modified cell comprises said first heterologous nucleic acid integrated into:

(i) a position within, or two positions that flank, a nucleotide sequence encoding the CRISPR/Cas endonuclease, or (ii) a position within, or two positions that flank, a transcription control element that is operably linked to a nucleotide sequence encoding the CRISPR/Cas endonuclease.

19. The genetically modified cell of any one of 11-18, wherein the genetically modified cell comprises a second heterologous nucleic acid comprising a second CRISPR/Cas target sequence that is different than said first CRISPR/Cas target sequence, wherein the second heterologous nucleic acid is integrated into:

(i) a position within, or two positions that flank, a nucleotide sequence encoding the CRISPR/Cas endonuclease, or (ii) a position within, or two positions that flank, a transcription control element that is operably linked to a nucleotide sequence encoding the CRISPR/Cas endonuclease.

20. The genetically modified cell of any one of 1-18, wherein the genetically modified cell is genetically modified with a second heterologous nucleic acid comprising a second CRISPR/Cas target sequence that is different than said first CRISPR/Cas target sequence.

21. The genetically modified cell of 20, wherein the second heterologous nucleic acid is integrated into a position that is within a protein-coding sequence, an RNA-coding sequence, or a transcription control element.

22. The genetically modified cell of 20 or 21, wherein the second heterologous nucleic acid is integrated into two or more positions within the genome.

23. The genetically modified cell of 22, wherein the second heterologous nucleic acid is integrated into two or more positions that (i) are within protein-coding sequences, RNA-coding sequences, or transcription control elements; or (ii) flank a protein-coding sequence, an RNA-coding sequence, or a transcription control element.

24. The genetically modified cell of 22 or 23, wherein the second heterologous nucleic acid is integrated into, or flanks, two or more different protein-coding sequences, RNA-coding sequences, or transcription control elements.

25. The genetically modified cell of any one of 22-24, wherein said second heterologous nucleic acid is integrated into at least two positions that are within 1 kilobase (1 kb) of one another.

26. The genetically modified cell of any one of 1-25, wherein the first CRISPR/Cas target sequence has a length in a range of from 17-22 nt.

27. The genetically modified cell of any one of 1-26, comprising:

(i) a CRISPR/Cas guide RNA comprising a guide sequence that is complementary to the first CRISPR/Cas target sequence, and/or (ii) a nucleic acid encoding said CRISPR/Cas guide RNA.

28. The genetically modified cell of any one of 19-25, comprising:

(i) a CRISPR/Cas guide RNA comprising a guide sequence that is complementary to the second CRISPR/Cas target sequence, and/or (ii) a nucleic acid encoding said CRISPR/Cas guide RNA.

29. A kit comprising:
a plurality of genetically modified cells according to any one of 1-26, wherein each cell of the plurality of cells comprises said first heterologous nucleic acid integrated into one or more different positions within the genome.

30. The kit of 29, further comprising:

(i) a CRISPR/Cas guide RNA comprising a guide sequence that is complementary to the first CRISPR/Cas target sequence, and/or (ii) a nucleic acid encoding said CRISPR/Cas guide RNA.

31. The kit of 29 or 30, further comprising: a CRISPR/Cas endonuclease, and/or a nucleic acid encoding said CRISPR/Cas endonuclease.

32. The kit of 29, further comprising one or more expression vectors encoding one or more of: (i) a CRISPR/Cas guide RNA comprising a guide sequence that is complementary to the first CRISPR/Cas target sequence, and (ii) a CRISPR/Cas endonuclease.

33. A kit comprising:

(i) a plurality of genetically modified cells according to any one of 19-25, wherein each cell of the plurality of cells comprises said first heterologous nucleic acid integrated into one or more different positions within the genome; and (ii) a CRISPR/Cas guide RNA, or a nucleic acid encoding said CRISPR/Cas guide, wherein the CRISPR/Cas guide RNA comprises a guide sequence that is complementary to the second CRISPR/Cas target sequence.

34. A method of generating the genetically modified cell of any one of 1-28, the method comprising:
incorporating the first heterologous nucleic acid into one or more positions within a parent cell's genome, thereby generating the genetically modified cell of any one of 1-28.

35. The method according to 34, wherein the parent cell is a bacterial cell, a fungal cell, an invertebrate cell, a vertebrate cell, or a mammalian cell.

36. The method according to 34 or 35, wherein the first heterologous nucleic acid comprises the PAM.

37. The method according to any one of 34-36, comprising incorporating the first heterologous nucleic acid into (i) a position within, or two positions that flank, a nucleotide sequence encoding a CRISPR/Cas endonuclease, or (ii) a position within, or two positions that flank, a transcription control element that is operably linked to a nucleotide sequence encoding a CRISPR/Cas endonuclease.

38. The method according to any one of 34-37, wherein the method comprises incorporating a second heterologous nucleic acid that comprises a second CRISPR/Cas target sequence that is different than the first CRISPR/Cas target sequence, into one or more positions within the parent cell's genome.

39. The method according to 38, wherein the method comprises incorporating the second heterologous nucleic acid into (i) a position within, or two positions that flank, a nucleotide sequence encoding a CRISPR/Cas endonuclease, or (ii) a position within, or two positions that flank, a transcription control element that is operably linked to a nucleotide sequence encoding a CRISPR/Cas endonuclease.

40. The method according to any one of 34-39, comprising incorporating a nucleotide sequence encoding a CRISPR/Cas endonuclease into the parent cell's genome.

41. The method according to any one of 37-40, wherein the CRISPR/Cas endonuclease (i) is a chimeric CRISPR/Cas fusion protein and/or (ii) has nickase activity or lacks nuclease activity.

42 The method according to any one of 37-41, wherein the CRISPR/Cas endonuclease is selected from: a class 2 CRISPR/Cas endonuclease, a Cas9 protein, a type V CRISPR/Cas endonuclease, a type VI CRISPR/Cas endonuclease, a Cpf1 protein, a C2c1 protein, a C2c3 protein, and a C2c2 protein.

43 The method according to 42, wherein the CRISPR/Cas endonuclease is a Cas9 protein.

44. The method according to any one of 37-43, wherein the nucleotide sequence encoding the CRISPR/Cas endonuclease is operably linked to a promoter.

45. The method according to 44, wherein the promoter is an inducible promoter.

46. A method of editing the genome of the genetically modified cell of any one of 1-28, the method comprising:

introducing into the genetically modified cell a CRISPR/Cas guide RNA, or a nucleic acid encoding said CRISPR/Cas guide RNA, wherein the CRISPR/Cas guide RNA comprises a guide sequence that is complementary to the first CRISPR/Cas target sequence.

47. The method of 46, wherein said introducing comprises inducing expression of the CRISPR/Cas guide RNA from a nucleic acid present in the genetically modified cell.

48. The method of 46 or 47, further comprising introducing into the genetically modified cell a CRISPR/Cas endonuclease, or a nucleic acid encoding said CRISPR/Cas endonuclease.

49. The method of 48, wherein said introducing comprises inducing expression of the CRISPR/Cas endonuclease from a nucleic acid present in the genetically modified cell.

50. The method of 48 or 49, wherein the CRISPR/Cas endonuclease (i) is a chimeric CRISPR/Cas fusion protein and/or (ii) has nickase activity or lacks nuclease activity.

51. The method of 49 or 50, wherein the CRISPR/Cas endonuclease is selected from: a class 2 CRISPR/Cas endonuclease, a Cas9 protein, a type V CRISPR/Cas endonuclease, a type VI CRISPR/Cas endonuclease, a Cpf1 protein, a C2c1 protein, a C2c3 protein, and a C2c2 protein 52. A genetically modified non-human multicellular organism, comprising the genetically modified cell of any one of 1-28.

53. The genetically modified non-human multicellular organism of 52, wherein the organism is a plant, a fungus, an invertebrate, a fly, a worm, a vertebrate, an insect, an arachnid, an algae, a helminth, a protozoan, a fish, a mammal, a rodent, an ungulate, or a non-human primate.

54. The genetically modified non-human multicellular organism of 53, wherein the organism is an insect.

55. The genetically modified non-human multicellular organism of 54, wherein the organism is a mosquito.

56. The genetically modified non-human multicellular organism of 53, wherein the organism is a mouse.

57. The genetically modified non-human multicellular organism of 53, wherein the organism is a plant.

58. The genetically modified non-human multicellular organism of 53, wherein the organism is an arachnid.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: mCAL: A Versatile Approach for Multiplex Action of Cas9 Using One sgRNA and Loci Flanked by Programmable Target Sequences The CRISPR/Cas gene editing methodology is being widely adopted across nearly every field of biology in academia, biotechnology, and pharmaceutical fields as it holds tremendous power and potential to revolutionize the manipulation of DNA in live organisms. One powerful application of the CRISPR/Cas endonuclease methodology is its ability to "multiplex" to different genomic targets within the same cell, ultimately allowing for targeted manipulation of many genes at once in massive parallel, rather than series. However, many of the same restrictions and limitations accompany the current approaches for targeting at multiple loci including (i) generation of multiple sgRNA-expressing cassettes, (ii) target site sequence identity and genomic location, (iii) modification of the integrating allele(s) to eliminate the target site, (iv) availability of PAM sequences, and (v) potential for similar "off-target" sequences to exist.

To address and circumvent many of these issues, the examples here demonstrate the development of a genetic system to demonstrate multiplexing the target sequence within the yeast genome allowing use of a single sgRNA with the Cas9 nuclease for both essential and non-essential genes. Furthermore, this system allows for either sequential (maintaining inducible Cas9 present in the genome) or simultaneous (scarless excision) manipulation of Cas9 itself. This methodology can be applied to any organism currently utilizing the CRISPR technology and can be applied conveniently to create genomic libraries, artificial genome sequences, and highly programmable strains or cell lines that can be rapidly (and repeatedly) manipulated at multiple loci with extremely high efficiency. The method is termed mCAL, for "Multiplexing of Cas9 at Artificial Loci."

Results

Design of a Novel Cas9 Multiplexing Strategy

Previous work has shown that Cas9 is able to recognize repeated sequences within the genome, including telomeres, repetitive sequences within exons and/or introns, and Ty retrotransposon delta sites when programmed by a single sgRNA sequence. Additionally, some of the restrictions for introduction of the DSB depend on the presence of a PAM sequence, the sequence content and identity of the genomic target, the local chromatin structure, and the potential for off-target effects if there is a similar sequence present elsewhere in the genome. To circumvent many of these restrictions, a system was developed, using *S. cerevisiae* as a model, to illustrate the utility of this unique application of Cas9-mediated gene editing in vivo. The mitotically expressed septin protein family was used as a proof of principle for this gene manipulation system. Four of the five mitotically-expressed septin proteins (CDC11, CDC12, CDC3, and CDC10) (HARTWELL 1971) whereas one is non-essential (SHS1) yet still contributes to function (IWASE et al. 2007; GARCIA et al. 2011; FINNIGAN et al. 2015). These proteins are well conserved across Eukarya (PAN et al. 2007) and were chosen as a proof of concept for the Cas9-based system demonstrated here because (i) the spectrum of subunits are all paralogous genes from a common ancestor and (ii) some are essential genes requiring additional cloning steps for genetic manipulation. At the genomic loci for both the CDC11 and SHS1 genes, unique, non-yeast 23 nucleotide sequences (20 bp target sequence with a 3' NGG PAM sequence) were introduced (see Materials and Methods) that had exceptionally few matches within the budding yeast genome flanking either the full-length gene or a deletion cassette (FIG. 1A,C). The addition of either 23 bps (or 24 bps to maintain reading frame) does not come with the risk of spontaneous recombination and excision from the yeast chromosome as this is far below the size required for HR between repeat sequences such as the *Salmonella* hisG repeats (ALANI et al. 1987) or any of the LTR retrotransposon Ty elements repeat sequences (NEUVEGLISE et al. 2002). Second, a cassette expressing S.p. Cas9 under an inducible promoter (GAL1/10) with a nuclear localization signal (NLS) (DICARLO et al. 2013) was integrated in this same strain at the endogenous HIS3 locus (Table 2; FIG. 1B).

TABLE 2

Yeast strains used in this study.

| Strain | Genotype | Reference |
|---|---|---|
| BY4741 | MATa leu2Δ ura3Δ met15Δ his3Δ | (BRACHMANN et al. 1998) |
| GFY-1517 | BY4741; NUP188::mCherry::ADH1(t)::S.p.HIS5 | This study |
| GFY-2002 | BY4741; cdc11Δ::[u1]::CDC11::[u1]; shs1Δ::[u1]::Hyg$^R$::[u1]; his3Δ::[u2]::prGAL1/10$^3$::S.p.Cas9::NLS::ADH(t)::Kan$^R$::[u2] + pJT1520 | This study |
| GFY-2003 | BY4741; cdc11Δ::[u1]::CDC11::[u1]; shs1Δ::[u1]::Hyg$^R$::[u1]; his3Δ::[u1]::prGAL1/10::S.p.Cas9::ADH(t)::Kan$^R$::[u1] + pJT1520 | This study |

For the GFY-1517 strain shown in Table 2, WT yeast was transformed with an amplified PCR product (from plasmid pJT2868) to mCherry tag the endogenous copy of NUP188, a nuclear envelope protein (AITCHISON et al. 1995; FABRE AND HURT 1997). The S.p.HIS5 gene is from fission yeast *S. pombe* (and functions in place of *S. cerevisiae* HIS3). Brachmann et al., 1998, Yeast 14: 115-132

For the GFY-2002 strain shown in Table 2, yeast strain GFY-153 (cdc11Δ::Kan$^R$+pRS316::CDC11) was transformed with the amplified CDC11 product (from pGF-IVL972) containing both flanking [u1] Cas9 sites in-frame with the ORF as well as 330 bps of 5' and 3' UTR and plated on synthetic complete media containing 5-FOA (to select for the integration of the [u1]::CDC11::[u1] copy and loss of the WT Cdc11-expressing URA3-based plasmid). The CDC11-expressing URA3 plasmid (pJT1520) was subsequently transformed back into the correct isolate. Second, SHS1 was deleted using a modified Hyg$^R$ deletion cassette (GOLDSTEIN AND MCCUSKER 1999) containing flanking [u1] sites (23 bps) upstream and downstream of the MX sequence (from pGF-IVL1026) with 500 bps of SHS1 UTR. Third, the HIS3 locus (his3Δ0) was repaired by amplifying a WT copy of S.c.HIS3 with 500 bps of flanking UTR by PCR (template was genomic DNA from THS4213) and selected on SD-HIS media. Fourth, the expression cassette for S.p.Cas9 (Cas9 from *S. pyogenes*; human codon bias; amplified from Addgene plasmid #43804) was integrated at the HIS3 locus by PCR amplifying the following fragment in two roughly equal sized pieces (of approximately 5 kB each) that overlapped within the Cas9 gene: prHIS3::[u2]::prGAL1/10::S.p.Cas9::ADH(t)::Kan$^R$::[u2]::HIS3-3'UTR (from pGF-IVL975) and selected on rich media containing G418. The Cas9 gene has the SV40 NLS signal (KALDERON et al. 1984) appended at its C-terminus. Following each chromosomal integration event, genomic DNA was purified, amplified by PCR, and confirmed by Sanger sequencing for all three manipulated loci (CDC11, SHS1, and HIS3) including 5' and 3' UTR and the presence of each [u1] and/or [u2] Cas9 target sites. 814 base pairs of the prGAL1/10 promoter in the GFY-2002 strain were used upstream of the initiator Met to overexpress Cas9. The GFY-2003 strain in Table 2 was created similarly to GFY-2002, but used a Cas9-expressing cassette containing the flanking [u1] sites rather than [u2] (amplified from pGF-IVL1027), but is otherwise isogenic.

Flanking the entire expression cassette was either the [u1] (SEQ ID NO: 1140) Cas9 target, or a second unique variant [u2] (SEQ ID NO: 1141) in an otherwise isogenic yeast strain (FIG. 1B). Since the CDC11 gene is essential, a "covering vector" expressing a WT copy was also present in these strains and harbored the URA3 auxotrophic marker that can be counter-selected on media containing 5-FOA (FIG. 1A).

FIG. 1. Programmed non-yeast Cas9 target sites at multiple loci in budding yeast (A) A haploid yeast strain was constructed to include identical Cas9 target sites (including an NGG PAM sequence) flanking the endogenous CDC11 and SHS1 loci (designated "unique Cas9 site 1"; [u1]). The [u1] site was placed in-frame (addition of 1 nucleotide to the 5' end of the 23 bp Cas9 target site) after the CDC11 initiator Met as well as prior to the stop codon. The SHS1 gene was deleted using the Hygromycin-resistance MX cassette and identical [u1] sites were placed upstream and downstream of the cassette sequence. Since CDC11 is an essential gene, a URA3-based CEN-plasmid was also present expressing a WT copy of CDC11 with no 3' UTR sequence. Red triangles designate the site of the Cas9-directed double-stranded break at the +3 position upstream of the PAM sequence. (B) Expression of the S.p.Cas9 gene product with a C-terminal SV40 NLS was integrated at the endogenous HIS3 locus in these strains under control of the yeast GAL1/10 promoter and ADH1 terminator sequences. In one strain variant (GFY-2002), the Cas9 cassette harbored a second unique Cas9 target site, [u2], whereas in a separate, otherwise isogenic strain (GFY-2003), the [u1] target site was also included flanking the entire locus. (C) The unique, non-yeast Cas9 target sites, [u1] and [u2], originated from the human SEPT9 and MMP23A loci, respectively, and displayed a very low level of sequence homology to the entire yeast genome. High-copy 2μ plasmids expressed the sgRNA [u1] or [u2] sequences under control of the constitutive yeast snoRNA SNR52 promoter and SUP4 terminator sequences.

Figure 6A:
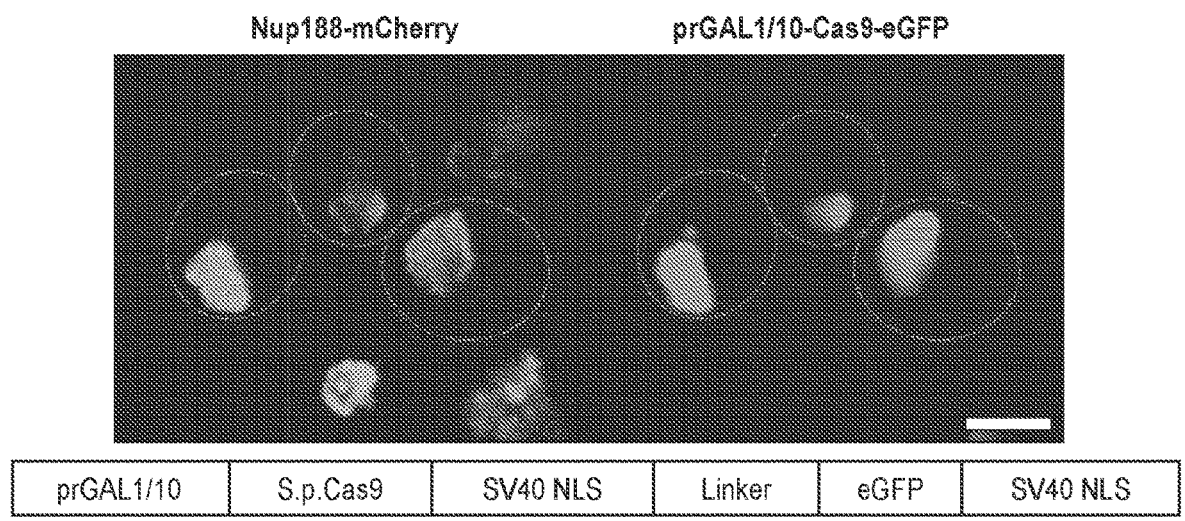
FIG. 6 (panels A-B) present data related to the expression of Cas9-eGFP in yeast and the non-toxicity of the tested exogenous [u1]/[u2]-Cas9 system in vivo.
Figure 6B:
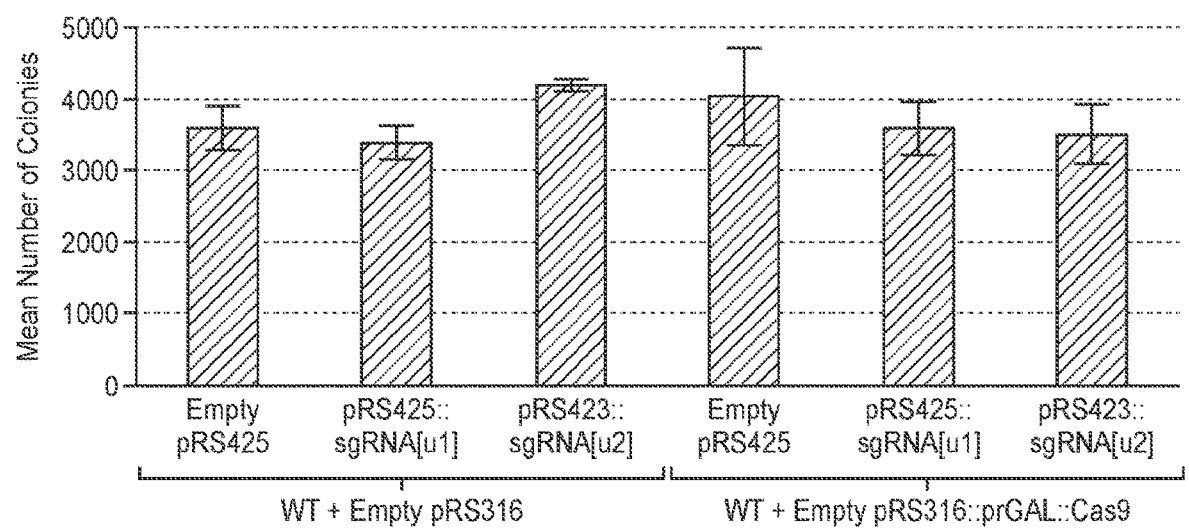
Figure 7A:
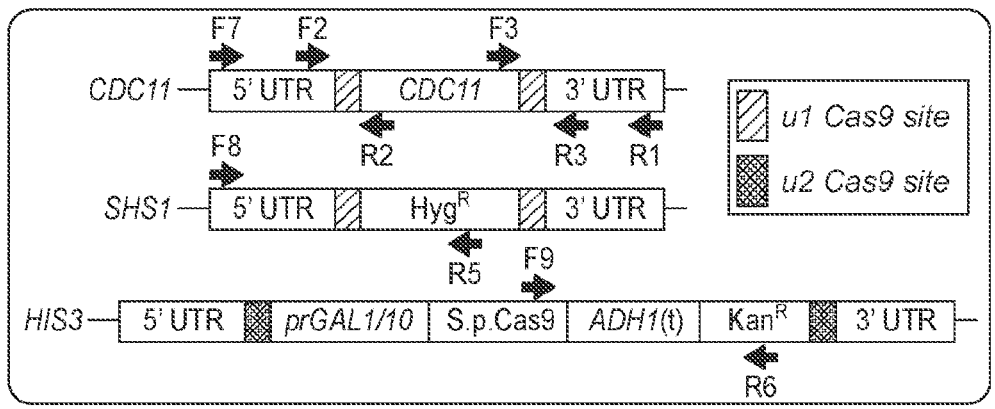
FIG. 7 (panels A-B) presents data related to the integration at either two of three genomic loci (including removal of Cas9 itself), using a single sgRNA[u1] system and only 30 base pairs of flanking homology in the donor polynucleotide.
Figure 7A:
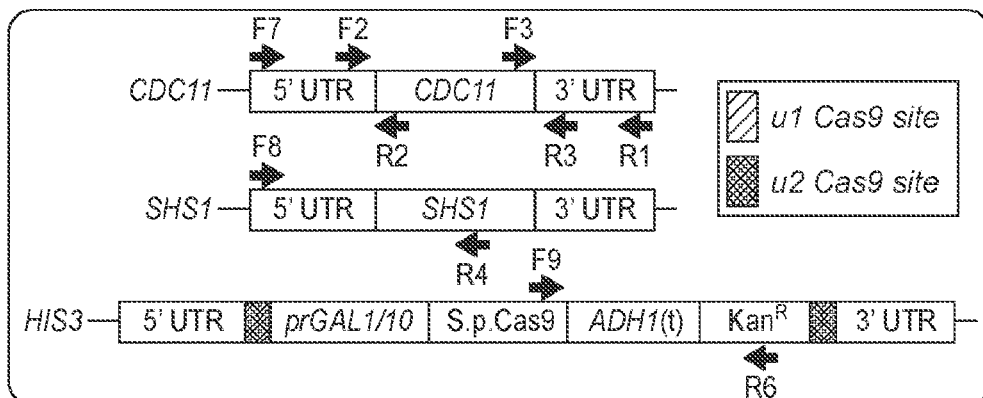
Figure 7A:
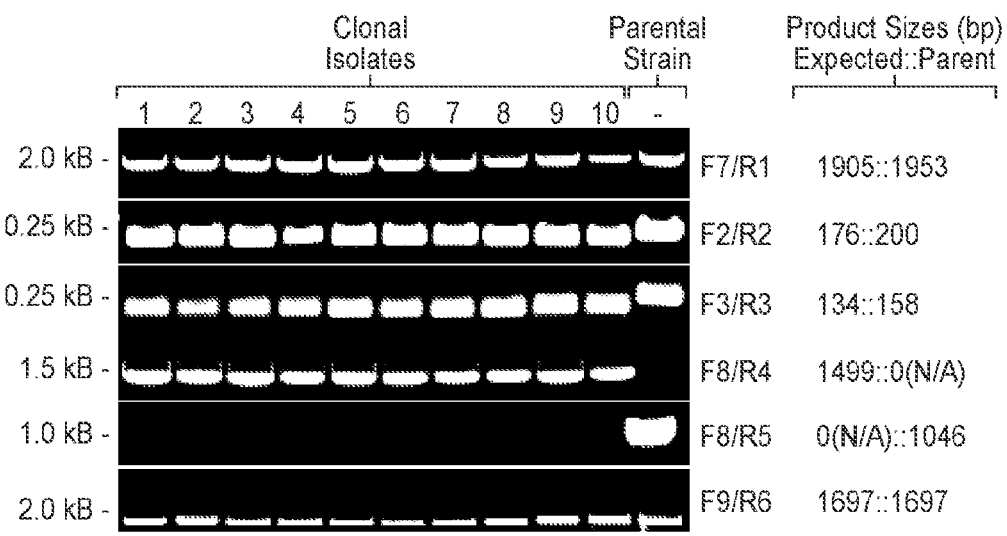
Figure 7B:
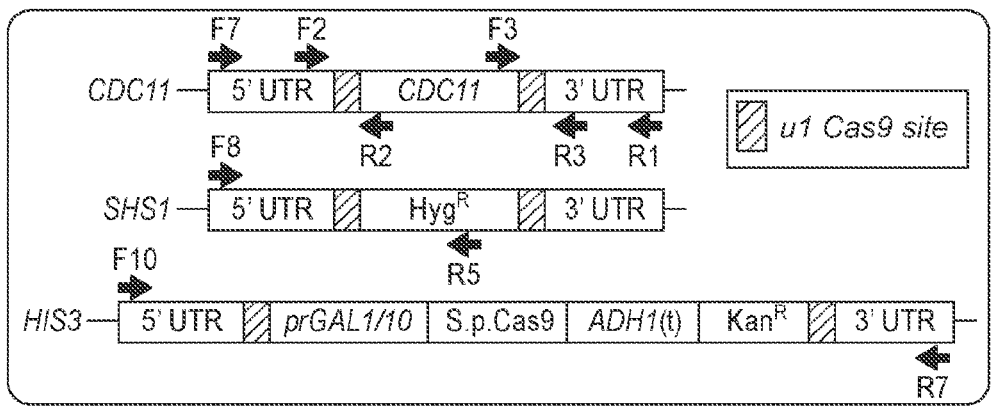
Figure 7B:
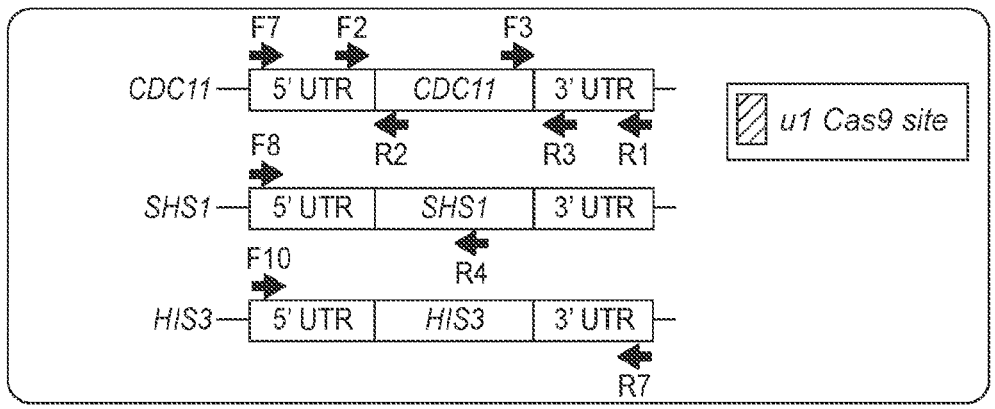
Figure 7B:
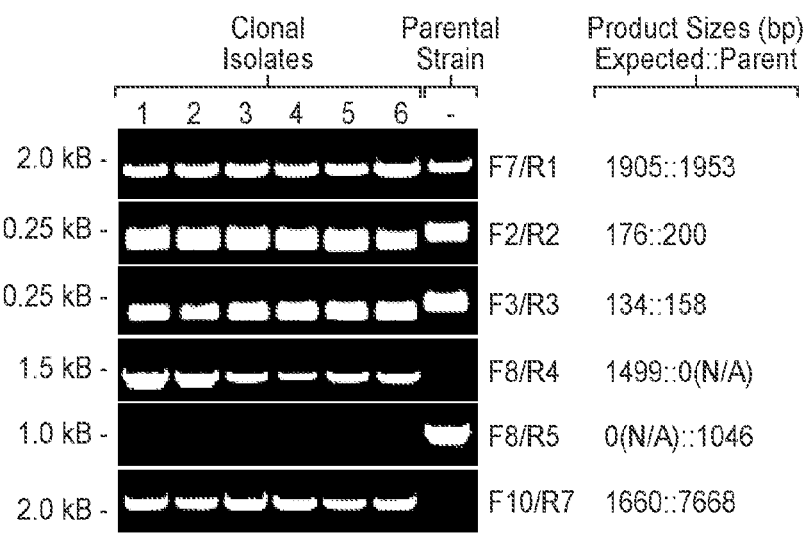

The rationale for the placement of flanking (as opposed to a single) genomic target site for Cas9-induced double stranded break (DSB) formation is to increase the efficiency and frequency of homologous recombination (HR) events between the chromosomal locus and the transformed PCR amplified product to integrate (see FIG. 5). This common strategy to multiplex Cas9 to more than one genomic target (within the same locus of interest) can assist in excising and, when appropriate, reprogramming entire regions (exons, introns, protein coding domains, splice sites, etc.). Removing the entire coding sequence (or deletion sequence) from the chromosomal loci of interest greatly reduces the possibility for inappropriate HR events and removes the need for codon alterations to either the integrated allele(s) and the WT covering vector to prevent Cas9 re-targeting to the final allele (see FIG. 5). Rather than design guide RNAs to each independent position, the method here involved using a single sequence to target Cas9 to all desired positions (in the two parental strains) to either four or six [u1] target sites. Thus, only a single sgRNA[u1]-expression construct on a high-copy plasmid is needed (FIG. 1B). In this system, and under the inducible GAL1/10 promoter, GFP-tagged Cas9 was both expressed and properly localized to the nucleus in yeast cells (FIG. 6A). Furthermore, expression of either Cas9, or the sgRNA[u1] or [u2] guides, or both together in otherwise WT cells (lacking the corresponding [u1] or [u2] sequences) yielded no detectible loss of transformation efficiency nor viability (FIG. 6B).

FIG. 5. Limitations of "classical" Cas9-mediated manipulation of essential genes. (A) Targeting an essential gene in vivo requires the presence of a WT-expressing "covering" plasmid that can be counter-selected (harboring URA3) by growth on media containing 5-FOA. Targeting the CDC11 gene at two genomic positions, [g1] (within the coding region) and [g2](within the flanking 3' UTR) requires that both 23 nucleotide sequences are not present within the WT copy of the covering plasmid expressing CDC11. Example Cas9 target site sequences are shown based on the proposed collection of target sites within the yeast genome. If the [g1] target sequence within CDC11 were used, the corresponding sequence of the covering vector would have to be mutated to prevent inappropriate targeting by Cas9 to the vector sequence. Synonymous changes could be made (red text) to the covering vector so as to not alter the amino acid sequence [v] with a priority to residues found within the PAM motif and directly upstream sequence (12 base pairs of the target site) as these are most significant for Cas9 target site "seeding". Since the covering vector does not contain 3' UTR to CDC11, no additional changes need to be made to allow for targeting at [g2] position within the terminator. However, it should be noted that 3'UTR sequences may pose difficult in finding suitable Cas9 target sites due to the AT-rich stretches, and the possibility for a TTTTTT sequence which can terminate RNA polymerase III transcripts and lower GC content within the target sequence. (B) If a single genomic target is used, [g1] or [g2], to create a double-stranded break (DSB) within the CDC11 locus, there are several scenarios that would allow for inappropriate crossover when integrating a mutant allele (red asterisk) in place of the WT endogenous copy. When using [g1], which is downstream of the proposed mutant allele, the crossover event could occur either upstream of the mutation within the promoter sequence (first panel) or downstream of the mutation within the coding sequence (second panel). The second event would repair the DSB but fail to integrate the mutant allele. Similarly, use of [g2] within the terminator sequence would also have the same issue with the possibility of the crossover event occurring downstream of the desired mutation. Thus, in order to optimize the integration efficiency of the mutant allele, one should (i) increase the 5' homology (promoter) sequence and/or (ii) choose a Cas9 target site as close to the mutation as possible to prevent repair of the WT gene copy as has been suggested by others. However, if the mutation is near the initiator Met within the coding sequence, or the gene is substantially large, then choosing a [g2] terminator target (which is not present within the covering vector) encounters the same efficiency issues. Therefore, programming Cas9 to target a specific position close to the desired mutation [g1] would increase integration efficiency but would also require changing the same target site within the covering vector sequence [v]. Furthermore, if multiple mutant alleles spanning the entire length of the gene were to be integrated, this strategy would either require multiple Cas9 genomic targets, or varying efficiencies based on the position of the desired mutation(s). Additionally, for essential genes, the presence of the covering vector creates an additional step (to mutate the WT gene sequence) to prevent Cas9-dependent targeting of this protective vector. (C) One possible solution is to target multiple positions within the locus of interest and create two DSBs, one of which is upstream of the mutation of interest within the coding sequence [g3]. In this way, recombination can only occur upstream and downstream of the two DSBs, and would efficiently introduce the desired allele with virtually no inappropriate crossover events (assuming efficient targeting by Cas9). However, since [g3] is still within the coding sequence, the [v] position within the covering vector would require alteration and rather than creating a single sgRNA construct, two constructs sgRNA[g2] and sgRNA [g3] would be required to manipulate this single locus. The amount of cloning required would be further increased if this strategy was extended to additional loci; targeting of three genes would require multiplexing 6 guide RNA cassettes and the covering vector sequences (example illustrated below). (D) Finally, integration of an essential gene allele using a traditional Cas9 approach requires yet another cloning step. If any genomic target is chosen within the coding sequence, [g1] or [g3] for instance, then the coding sequence of the integrated allele itself at these same position(s) must also be altered so as to prevent Cas9-mediated targeting of the final integrated allele. Therefore, at minimum, a single guide [g1] strategy requires (i) alteration of the covering vector, (ii) alteration of the mutant allele itself, and allows for (iii) inappropriate cross over between the mutant allele and [g1] target site, and (iv), would likely have to be altered for various alleles or constructs spanning the length of the target gene. A two-guide strategy, [g2] and [g3], which removes the possibility of inappropriate cross over, requires the same cloning alterations including the vector, the integrated allele itself, and design and construction of two sgRNA cassettes. These traditional strategies are laborious, suboptimal, and require the separate manipulation of many vectors outside of the Cas9/sgRNA system.

FIG. 6. Expression of Cas9-eGFP in yeast and the non-toxicity of the exogenous [u1]/[u2]-Cas9 system in vivo. (A) Yeast expressing Nup188-mCherry (GFY-1517; marker for the nuclear envelope) were transformed with a plasmid (pGF-IVL977) expressing S.p.Cas9 with an SV40 NLS sequence (SRADPKKKRKV) (SEQ ID NO: 1156), a flexible SGGGSG (SEQ ID NO: 1157) linker, eGFP, and a second SV40 NLS under control of the GAL1/10 promoter. Yeast were grown overnight in S+Raff/Suc-LEU, back-diluted to YP+GAL for a three hour induction at 30° C., and imaged by fluorescence microscopy. Representative cells are shown (scaled identically); white dotted lines mark the cell periphery. Scale bar, 2 µM. (B) Expression of Cas9, or the sgRNA[u1] or sgRNA[u2] cassettes, or both together, did not result in a significant loss of transformation efficiency and viability of the resulting yeast colonies. WT yeast (BY4741) were first transformed with either an empty pRS316 vector or a pRS316::prGAL1/10::Cas9 vector (pGF-V789). Next, yeast were grown overnight in S+Raff/Suc-URA media to saturation, back-diluted to YP+GAL for 5 hours at 30° C., and transformed with equal amounts (1-2 µg) of empty pRS425, pRS425::sgRNA[u1], or pRS423:: sgRNA[u2] vectors, recovered overnight in YP+GAL and plated onto SD-URA-LEU (for pRS425 vectors) or SD-URA-HIS (for pRS423 vectors). Experiments were performed in triplicate; colonies were counted and the average colony number was plotted for each genotype (error bars, SEM). There was no significant difference between WT yeast (first strain; unpaired t-test p-value=0.59) and yeast over-expressing Cas9 (fourth strain). Similarly, there was no difference between expression of the guide RNA[u1] alone (second strain) compared to co-expression of Cas9 (fifth strain; p-value=0.67). Similarly, there was no significant difference with or without Cas9 for the sgRNA[u2] constructs (third and sixth strains; p-value=0.18). These data suggest that (i) Cas9 expression is not toxic in yeast as has been previously reported, and (ii) neither the [u1] or [u2] RNAs are toxic to yeast (nor have obvious off-target locations within the yeast genome).

Multiplexing Cas9 to Programmed Genomic Target Sequences Using a Single sgRNA

Figure 2A:
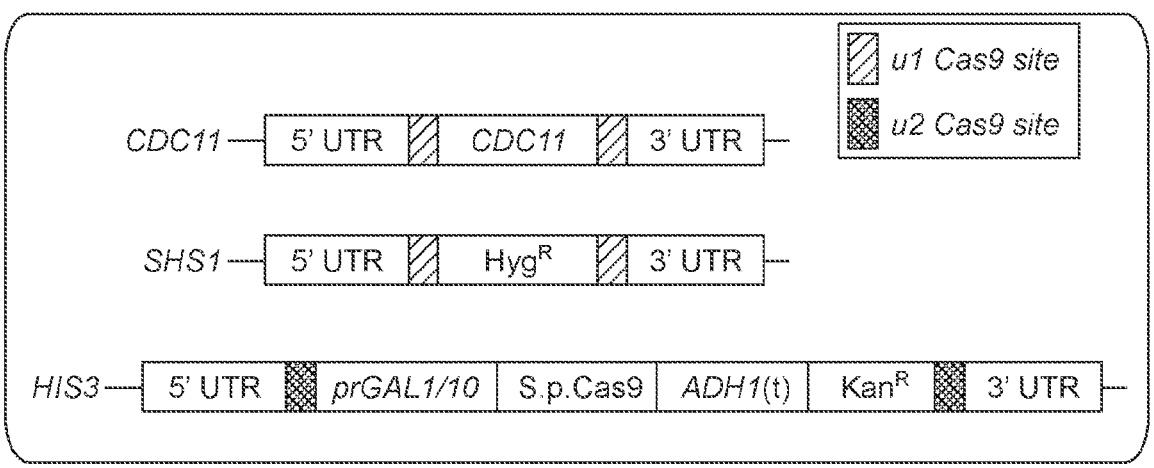
FIG. 2 (panels A-D) present schematic illustrations and data related to multiplexing Cas9 target sites, scarless integration at multiple loci including an essential gene, and optional simultaneous removal of Cas9 itself.
Figure 2A:
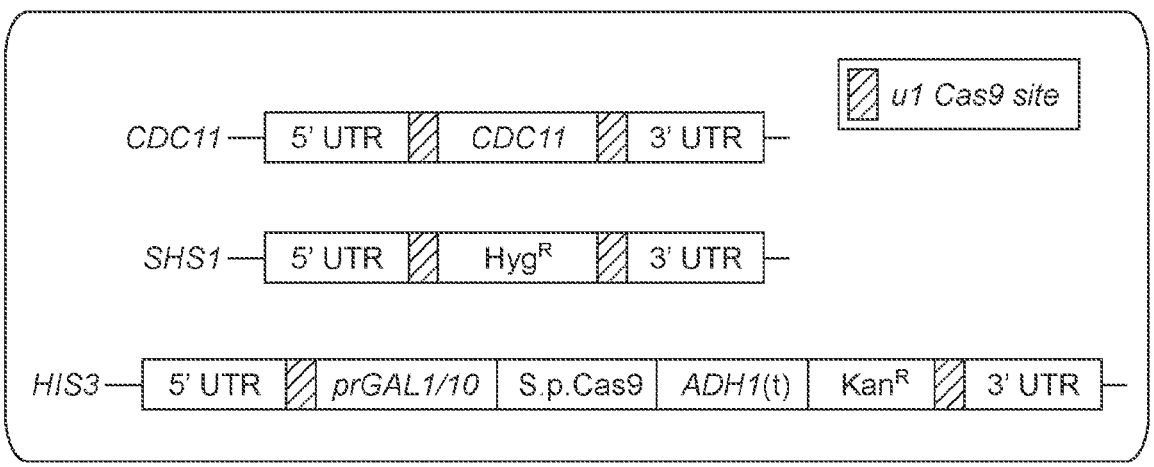
Figure 2B:
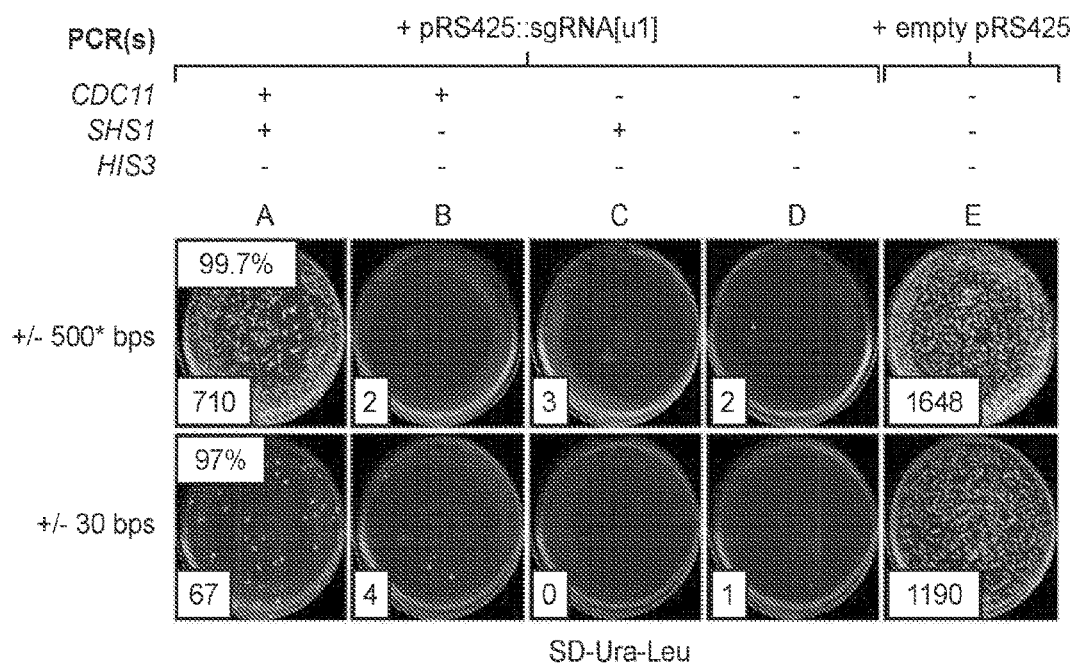
Figure 2B:
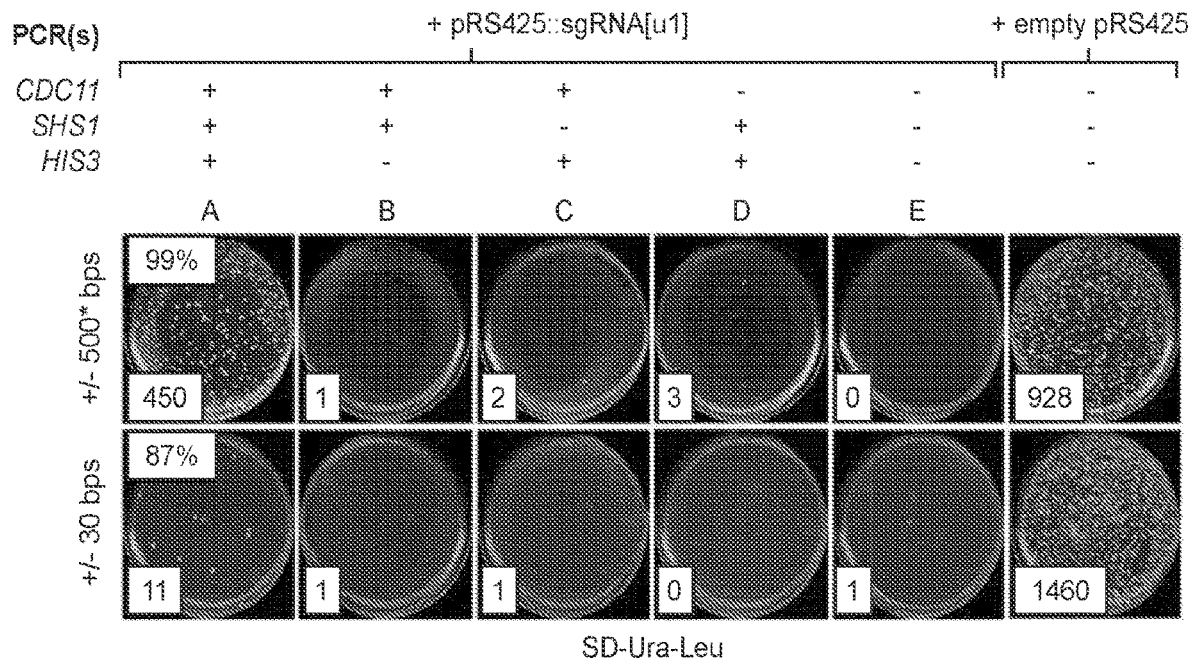
Figure 3A:
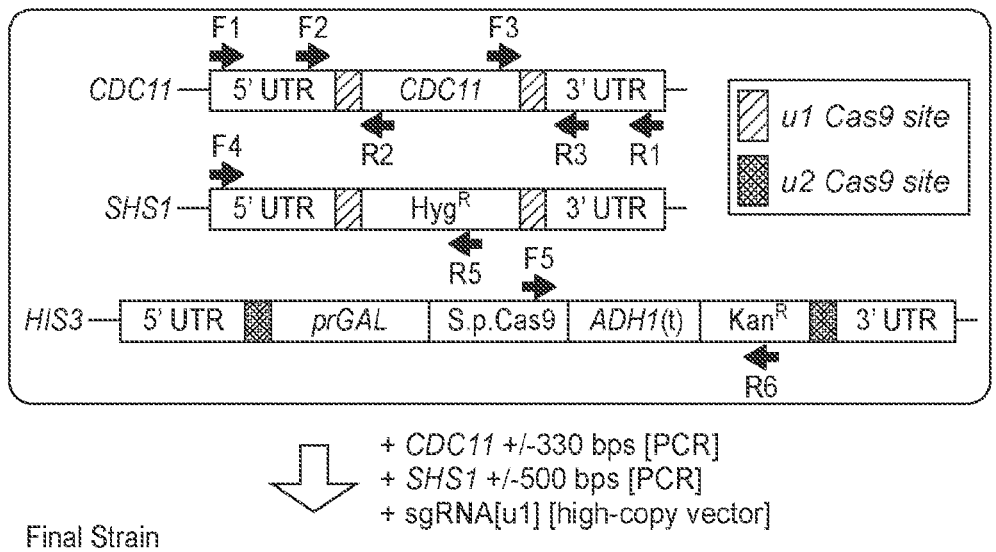
FIG. 3 (panels A-B) present schematic illustrations and data related to testing the efficiency of multiplexed targeting of two or three endogenous loci including removal of the Cas9 expression cassette.
Figure 3A:
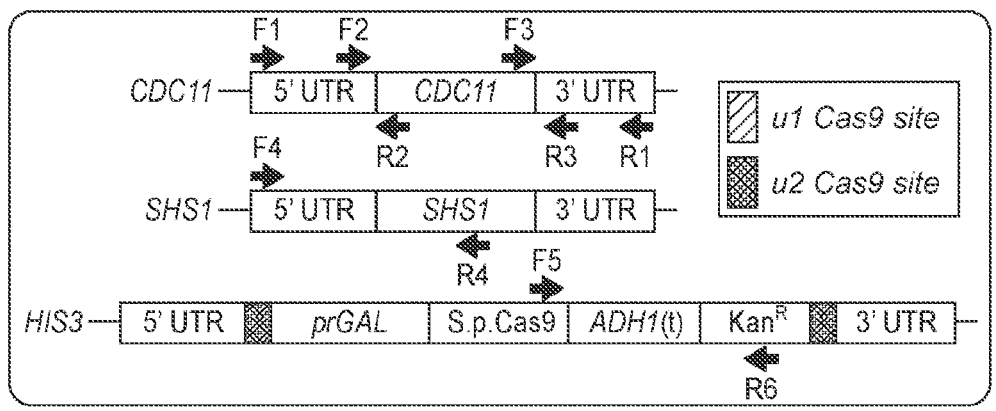
Figure 3A:
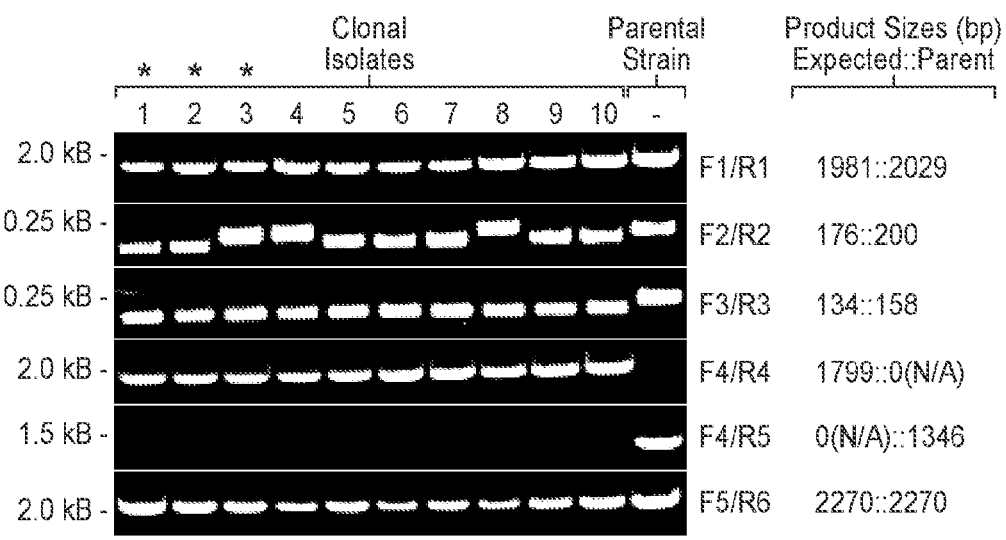
Figure 3B:
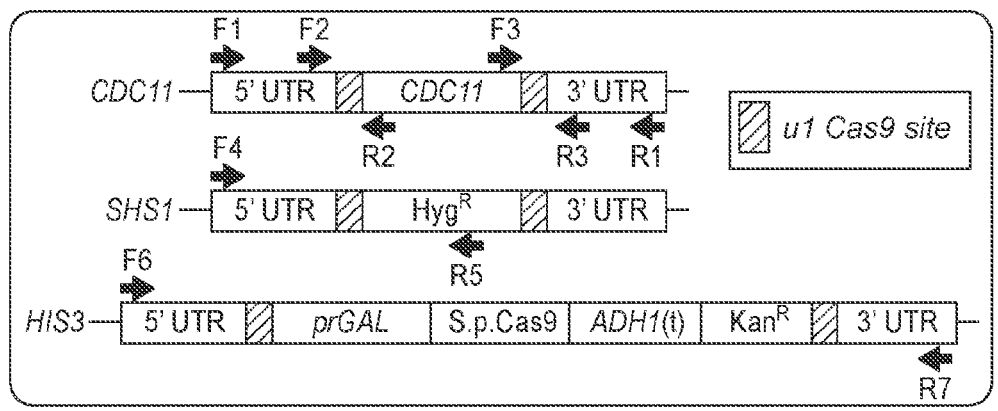
Figure 3B:
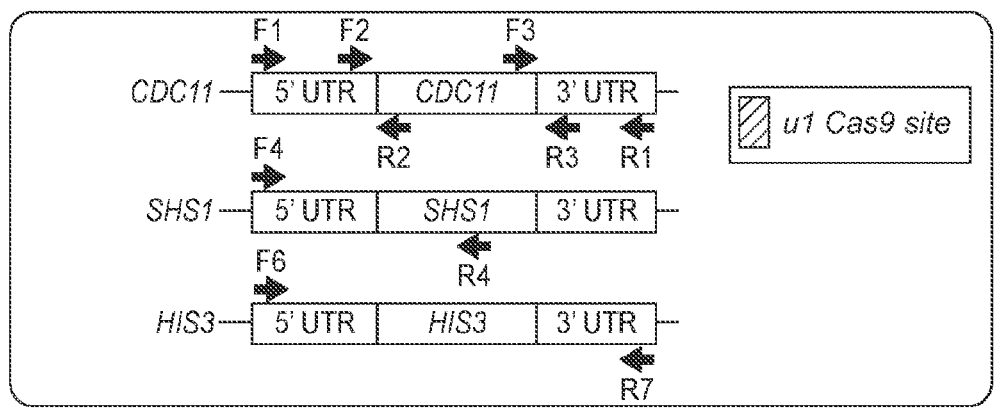
Figure 3B:
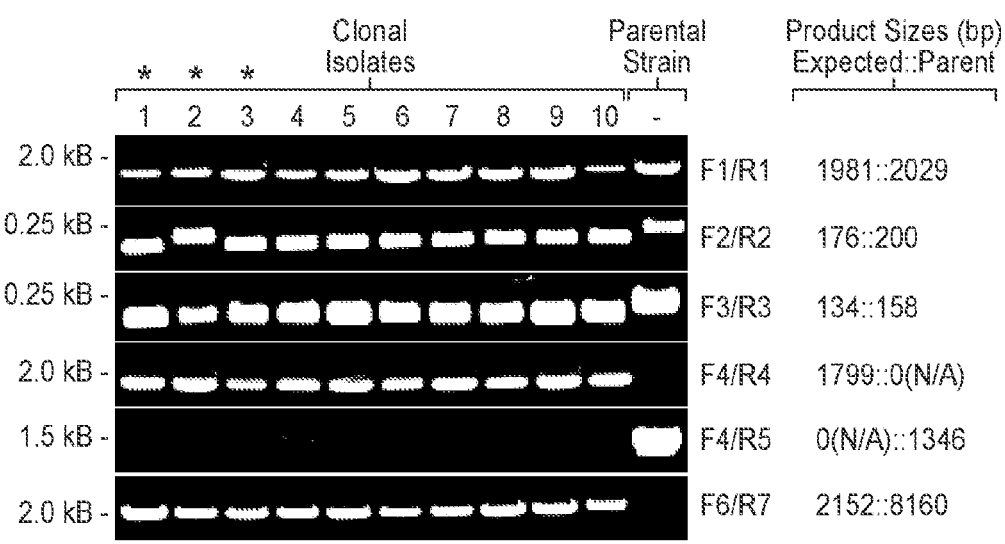
Figure 5A:
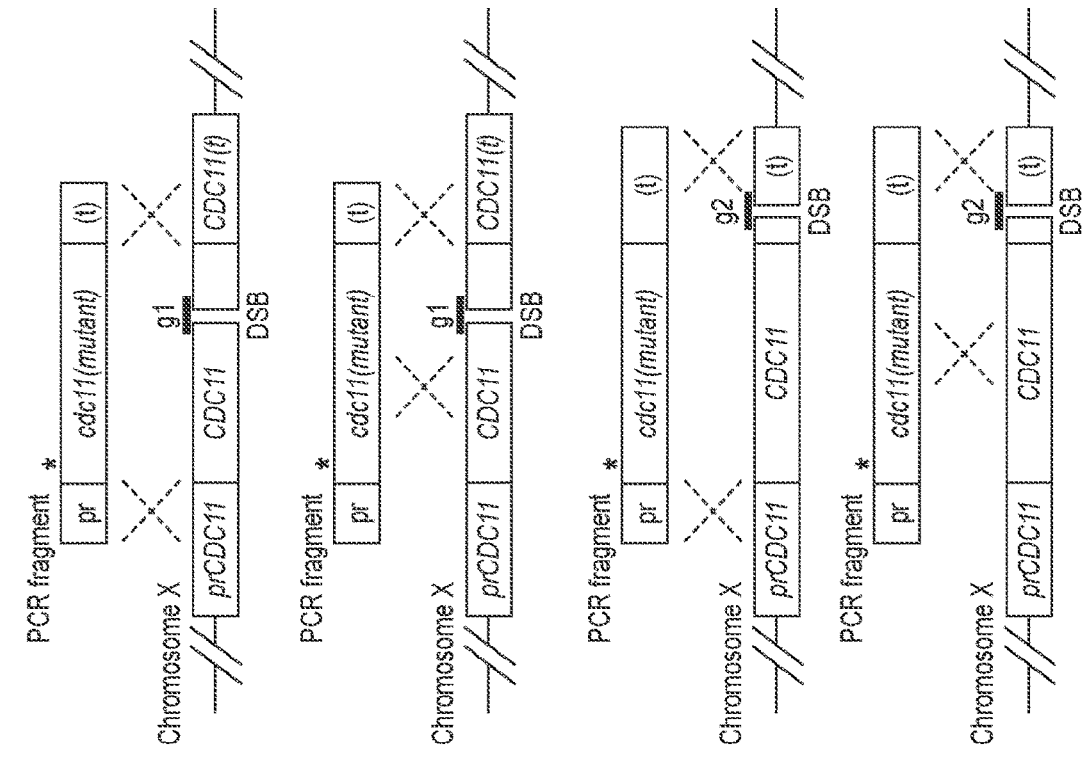
FIG. 5 (panels A-D) illustrate limitations of "classical" Cas9-mediated manipulation of essential genes.
Figure 5B:
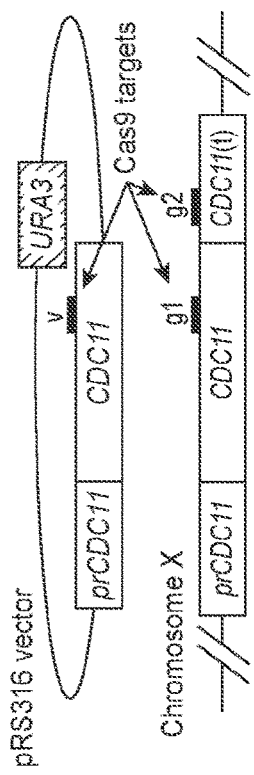
Figure 5C:
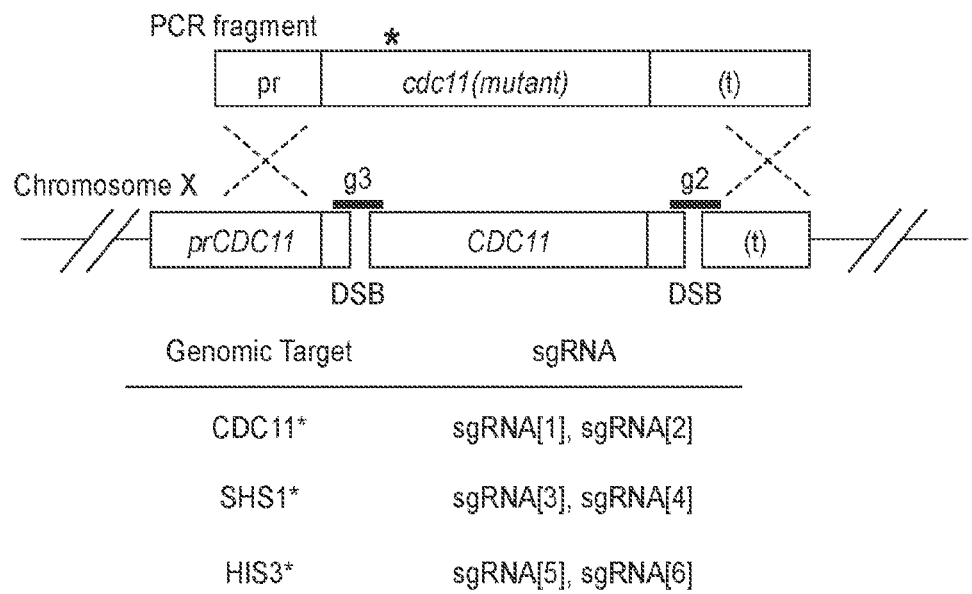
Figure 5D:
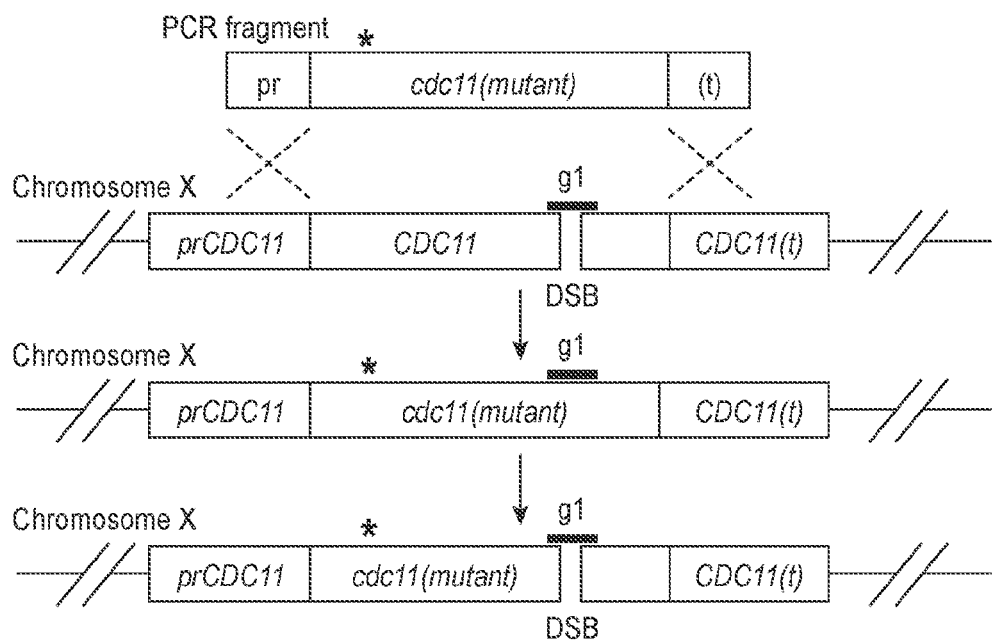

The two strains constructed, GFY-2002 and GFY-2003, allowed for simultaneous manipulation of the CDC11/SHS1 or CDC11/SHS1/HIS3 loci, respectively (FIG. 2A). Following induction of Cas9, yeast were transformed with the high-copy sgRNA[u1]-containing plasmid and combinations of amplified PCR fragments to integrate at each locus (FIG. 2B). Control reactions were also performed that were missing one or more PCRs (e.g. GFY-2002 "B" included only the CDC11 PCR fragment and not the SHS1 fragment) including reactions missing either Cas9 expression or the sgRNA cassette (Table 3). The PCR fragments had either 500 bps of flanking sequence homology to the genomic target (FIG. 2B, top plates), or 30 bp tails to be used for HR (FIG. 2B, bottom plates). For the GFY-2003 strain, the entire HIS3 locus was also repaired, removing the Cas9-expression cassette entirely. Targeting of Cas9 to the multiplexed [u1] genomic sites allowed for a highly efficient system: compared to control strains (which would have exposed DSBs with no corresponding PCR fragment(s) to repair from), this system showed between 300-500-fold increase in the number of viable colonies (Experiments labeled "A"). While this number was reduced when the size of the homologous tails for HR was limited to only 30 bps, a 10-50-fold increase was still seen.

TABLE 3

Transformation efficiency of control experiments lacking either Cas9 expression or sgRNA expression in vivo.

| Yeast Strain | Growth Condition | Plasmid transformed | Colonies |
|---|---|---|---|
| GFY-2002 | Galactose | Empty pRS425 | $1614^2$ +/− 427 (n = 7) |
| GFY-2002 | Dextrose | pRS425::sgRNA[u1] | 6025 +/− 4260 (n = 2) |

TABLE 3-continued

Transformation efficiency of control experiments lacking either Cas9 expression or sgRNA expression in vivo.

| Yeast Strain | Growth Condition | Plasmid transformed | Colonies |
|---|---|---|---|
| GFY-2003 | Galactose | Empty pRS425 | 1310 +/− 186 (n = 7) |
| GFY-2003 | Dextrose | pRS425::sgRNA[u1] | 5996 +/− 4239 (n = 2) |

As shown in Table 3, yeast cultures were grown overnight in S+Raff/Suc-URA, back diluted (to an $OD_{600}$ of roughly 0.3) in YP+GAL and incubated for 5 hours at 30° C. Equal amounts (1-2 μg) of empty pRS425 vector or pRS425:: sgRNA[u1] were transformed using a modified lithium acetate protocol (Eckert-Boulet et al. 2012) and recovered overnight in YP+GAL media prior to plating onto SD-URA-LEU plates. Colonies from each experimental trial were counted after a 3-day incubation at 30° C. For growth conditions, galactose-containing media induced expression of Cas9 whereas dextrose-containing media inhibited Cas9 expression. Colony number was estimated by plating several dilutions (1:10, 1:20, 1:100, etc.) to selective plates and the average total colony count was reported. The Error presented as Standard Error of Mean (SEM) The number of independent experimental trials is represented as "n".

The two designed strains allowed for either sequential (GFY-2002), or simultaneous (GFY-2003) removal of the Cas9-expression system itself. If subsequent Cas9-dependent integration (or deletion) events are required, then repressed (on media containing dextrose) Cas9 can remain at the HIS3 locus until removal is necessary or desired. In this way, a second sgRNA[u2] cassette was programmed to rapidly and cleanly excise Cas9 from the genome with no required oligonucleotides or PCR products. Fortuitously, the high copy pRS423 plasmid (Table 4) that expresses the sgRNA[u2] sequence also harbors the WT budding yeast HIS3 gene with a significant amount of flanking UTR (FIG. 2D). Therefore, the sgRNA-expressing plasmid serves as the source of dsDNA to repair the HIS3 locus and remove Cas9 (FIG. 2D) in a separate, highly efficiency transformation and integration event following manipulation of the CDC11/SHS1 loci. The high-copy plasmids used to express the guide RNAs are rapidly lost when not subjected to selection for the appropriate markers (Table 5). In this way, the entire Cas9-based system can be completely removed from the yeast genome either simultaneously or sequentially with other desired genetic manipulations.

TABLE 4

Plasmids used in this study.

| Plasmid | Description | Reference |
|---|---|---|
| pRS425 | 2μ; LEU2 AMP | (CHRISTIANSON et al. 1992) |
| pRS423 | 2μ; HIS3 AMP | (CHRISTIANSON et al. 1992) |
| pRS316 | CEN; URA3 AMP | (SIKORSKI AND HIETER 1989) |
| pSB1/JT1520 | CEN; URA3 AMP; prCDC11::CDC11[1] | (VERSELE et al. 2004) |
| pGF-V796 | pRS425; sgRNA[u1] | This study |
| pGF-V798 | pRS423; sgRNA[u2] | This study |
| pGF-IVL977 | prHIS3::[u2]::prGAL1/10::S.p. Cas9::NLS::Linker::eGFP::NLS::ADH(t)::Kan$^R$::[u2]::HIS3-3'UTR | This study |
| pGF-V789 | pRS316; prGAL1/10::S.p.Cas9::NLS::CDC10-3'UTR | This study |

For the prCDC11::CDC11 in plasmid pSB1/JT1520 (Table 4), there is no CDC11 3' UTR present within this vector. For plasmid pGF-V796, the sgRNA[u1]-expressing cassette is under control of the snoRNA SNR52 promoter and SUP4 terminator sequences (DiCarlo et al. 2013). The [u1] target sequence is CGGTGGACTTCGGCTACGTA (SEQ ID NO:1158). The entire sgRNA-expressing cassette was synthesized (GenScript, Piscataway, N.J.) with flanking BamHI and XhoI restriction sites (into a pUC57 vector) and subcloned to pRS425 followed by sequence verification. Christianson et al. 1992, Gene 110: 119-122; Sikorski and Hieter, 1989. Genetics 122: 19-27; Versele et al., 2004. Mol Biol Cell 15: 4568-4583.

For the pGF-V798 vector (Table 4), the sgRNA[u2]-expressing cassette was mutated from the [u1] sequence within pUC57 through successive rounds of PCR mutagenesis (ZHENG et al. 2004) to generate a [u2] target sequence of GCTGTTCGTGTGCGCGTCCT (SEQ ID NO: 1159) followed by a final subclone to the pRS423 vector.

The pGF-IVL977 vector (Table 4) was constructed by first creating a parent vector by in vivo ligation and homologous recombination in yeast (Finnigan and Thorner 2015) of the genotype: prHIS3::[u2]::prGAL1/10::NotI restriction site::ADH1(t)::KanR:[u2]::HIS3-3' UTR (pGF-IVL974). Next, a second round of in vivo ligation in yeast was used to insert the S.p. Cas9::NLS::Linker::eGFP::NLS sequence. The flexible linker has the sequence SGGGSG (SEQ ID NO: 1160) and the SV40 NLS sequence (Kalderon et al. 1984) is SRADPKKKRKV (SEQ ID NO:1161) and is found after both the Cas9 and eGFP sequences. A similar construct (pGF-IVL976) with only a single SV40 NLS present between Cas9 and a C-terminal eGFP tag did not yield as strong of a fluorescent signal within yeast cell nuclei compared to the pGF-IVL977 construct containing two SV40 nuclear localization signals under identical induction and growth conditions.

The pGF-V789 vector (Table 4) was constructed first by in vivo ligation in pRS315 to fuse the prGAL1/10 promoter, Cas9 gene, CDC10 3'UTR terminator (465 bps), and the Kan$^R$ cassette with a unique SpeI site present between the terminator and drug cassette. A unique NotI site (upstream of the prGAL1/10 sequence) was used to subclone the prGAL1/10::Cas9::NLS::CDC10(t) sequence to the same sites in pRS316 to yield pGF-V789.

FIG. 2. Multiplexing Cas9 target sites, scarless integration at multiple loci including an essential gene, and optional simultaneous removal of Cas9 itself (A) Two otherwise isogenic yeast strains contain six programmed Cas9 target sites within the genome flanking three distinct genomic loci. In GFY-2002, both CDC11 and SHS1 contained the [u1] sequence whereas the HIS3 locus (expressing Cas9) contained the [u2] sequence. In GFY-2003, the same three loci are all flanked by the [u1] sequence. (B) Yeast were induced for Cas9-expression followed by a transformation with various combinations of the high-copy vector expressing the sgRNA[u1] cassette and multiple PCR fragments to one or more of the targeted genomic loci. An empty pRS425 vector (far right panels) was used to illustrate the efficiency of transformation and selection for two plasmids using this protocol. Following a recovery phase in rich media containing galactose (to continually overexpress Cas9), yeast were plated onto SD-URA-LEU media for three days at 30° C., plates were imaged, and the total colony count for a representative plate was determined (white numbers). Two experimental variations were performed (in triplicate) using amplified PCR products with either 500 bps of flanking UTR homology (top plates) or 30 bps flanking UTR (bottom plates). For the CDC11 PCR product, 330 bps of flanking UTR was used (asterisk). For experiments labeled "A", which contained all of the necessary PCR products to each manipulated genomic target, a sample of individual colonies was tested on various growth conditions to ascertain whether the selectable marker(s) had been properly deleted or introduced (e.g. for replacement of shs1Δ::Hyg$^R$ to SHS1 WT, the loss of hygromycin resistance was tested; for replacement of Cas9 at the his3Δ locus, loss of G418 resistance and gain of SD-HIS resistance was tested for strain GFY-2003). The percentage shown (top left, red) illustrates the proportion of tested colonies that harbored all of the necessary selection marker(s) for each strain: GFY-2002-A (top, 5 independent trials, n=334 colonies sampled; bottom, 3 independent trials, n=213 colonies) and for GFY-2003-A (top, 5 trials, n=364 colonies; bottom, 3 trials, n=30 colonies). Since no marker(s) were associated with the CDC11 locus, this was excluded from this analysis. (C) The average colony count for all experimental trials is shown. Error, SEM. (D) In strain GFY-2002, the second [u2] sites flank the Cas9-expression cassettes at the HIS3 locus. The sgRNA[u2]-expressing cassette is present within the pRS423 vector and the selection marker is the S. cerevisiae HIS3 gene with 5' (317 bps) and 3' (201 bps) of flanking UTR. Therefore, transformation of the pRS423::sgRNA[u2] vector is sufficient to (i) target Cas9 to its own flanking [u2] sites, and (ii) serve as the source of the repaired WT HIS3 gene to integrate at the endogenous locus. Yeast whose CDC11 and SHS1 loci were repaired in (B), (GFY-2002 Experiment A), were transformed with either an empty pRS423 vector or the pRS423::sgRNA[u2] vector and selected on SD-URA-HIS plates (colony counts are shown). Colonies from either transformation event were tested for loss of G418 resistance and loss of the entire Cas9-expression cassette. The percentage shown refers to the number of colonies with the proper growth profile as in (B) (For the empty vector control, n=200 colonies in three trials, and for the pRS423::sgRNA[u2] experiment, n=196 colonies in triplicate).

Confirmation of Integrated Alleles at Multiple Loci

Figure 8:
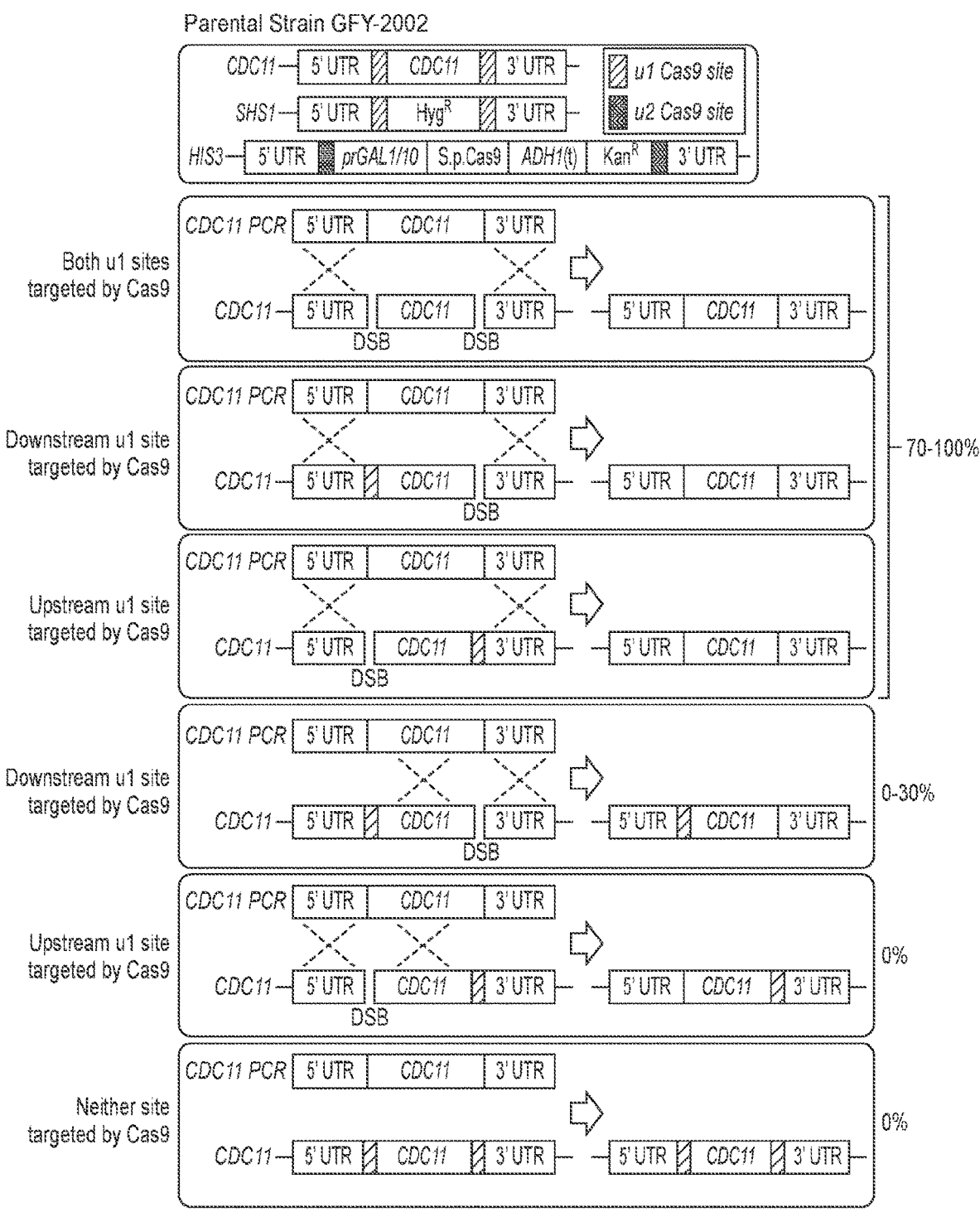
FIG. 8 presents possible outcomes of incomplete Cas9-targeting of [u1] sites at the CDC11 locus in vivo.
Figure 9A:
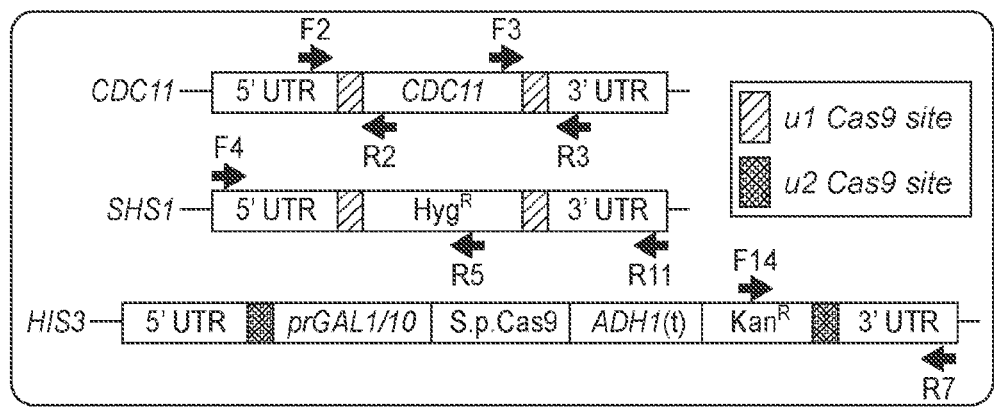
FIG. 9 (panels A-B) present analysis of surviving (very rare) isolates for control experiments missing one or more PCR fragments for integration.
Figure 9A:
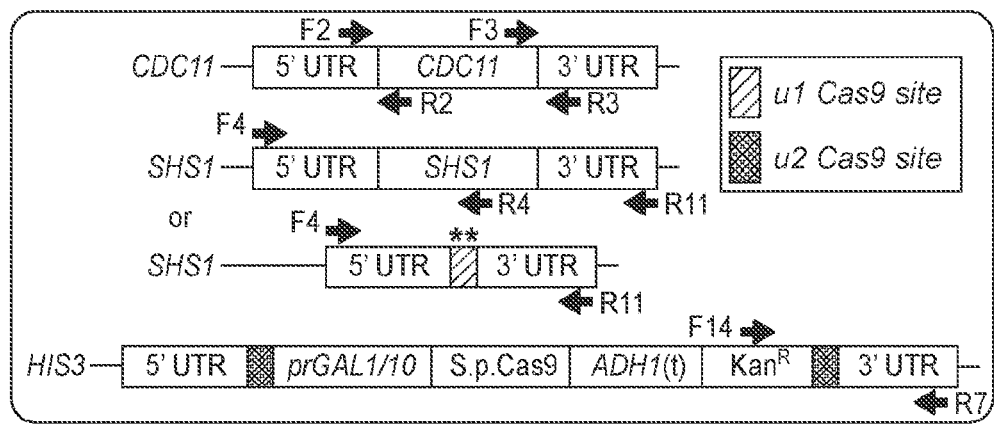
Figure 9B:
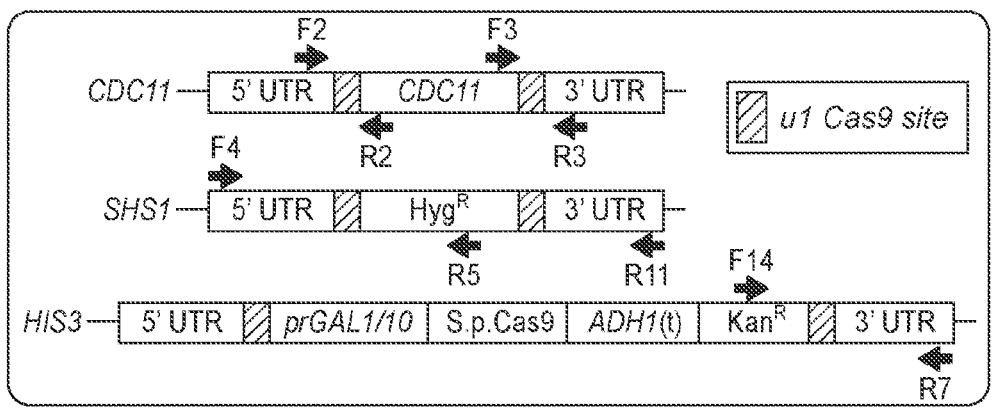
Figure 9B:
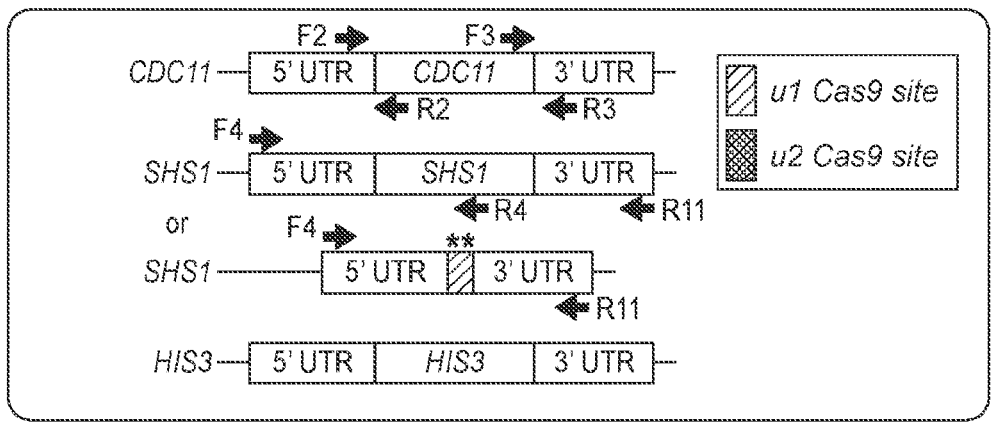
Figure 9B:
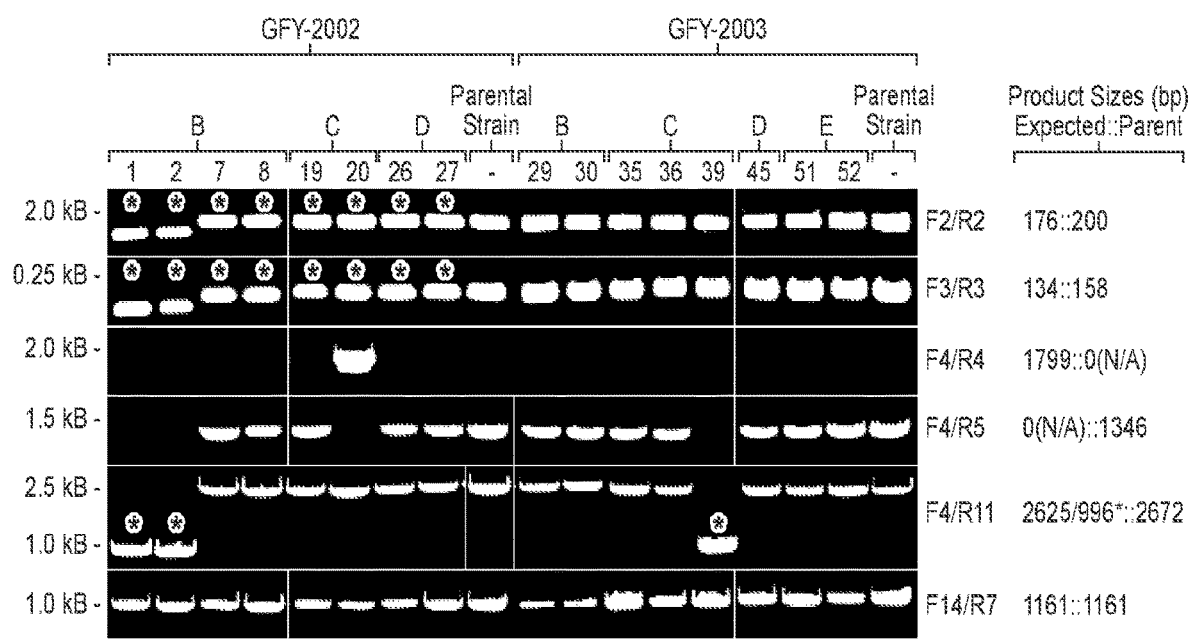

Viable strains from FIG. 2 were subjected to diagnostic PCR and DNA sequencing to determine whether each integration event had occurred at the desired loci (FIG. 3). PCRs were performed on each locus to ascertain whether the [u1] sites were properly removed (at the CDC11 locus), or, in the case of SHS1, the presence of the WT gene and loss of the Hyg$^R$ cassette. For strain GFY-2002, all tested isolates still harbored the Cas9-expression cassette and had properly integrated a WT SHS1 gene (FIG. 2B, left). Also, 7/10 isolates properly removed both [u1] sites at the CDC11 locus and this was confirmed by DNA sequencing. For strain GFY-2003, all isolates tested successfully integrated both the WT SHS1 gene and the HIS3 gene to replace the Cas9-expression cassette, and only 1/10 isolates left the upstream [u1] site unperturbed. Diagnostic PCRs were also performed on viable isolates that only used 30 bps of homology within the integrated PCR fragments with similar results (FIG. 7). Of the possible explanations for the remaining [u1] site near the initiator Met of CDC11, a major contributor may have been the design of the integration event. While both the SHS1 and HIS3 loci were completely replaced (and had no homology to the chromosomal allele present), the CDC1 copy to be integrated shared homology across the entire CDC11 coding sequence with the integrated allele except for the [u1] sites (FIG. 8). In all isolates tested by diagnostic PCR (from all experimental trials), The upstream [u1] site was found to only be present in 4/36 strains (FIG. 3, FIG. 7). To increase the efficiency of this system even further, several modifications could be made including (i) starting with a cdc11Δ null allele in the genome (covered by a WT plasmid) or (ii) altering the codon bias or gene structure of the allele to be integrated to minimize the potential inappropriate HR that can occur between the two copies (FIG. 8).

FIG. 3. Testing the efficiency of multiplexed targeting of two or three endogenous loci including removal of the Cas9 expression cassette. (A) Clonal isolates from transformation (using 500 bps flanking homology) of the GFY-2002 strain, which was used to replace both the CDC11 and SHS1 loci (leaving the HIS3 locus unaltered), were tested by diagnostic PCR and DNA sequencing. An identical analysis was performed on isolates that used 30 bps flanking homology (FIG. 7). Following confirmation by the presence/absence of nutritional and/or drug resistance markers (FIG. 2B), ten randomly selected isolates were selected for further analysis. Chromosomal DNA was purified (AMBERG et al. 2006) and diagnostic PCRs were performed and visualized on agarose gels to ascertain the status of each manipulated locus and the presence (or absence) of the [u1] sites compared to the parental strain. For CDC1 (top three gels), the entire locus was amplified (primers F1/R1) as well as small fragments flanking the upstream (F2/R2) or downstream (F3/R3) [u1] sites to determine if the 24 bp Cas9 target site was still present. For SHS1 (fourth and fifth gels), PCRs were performed using unique primers to either SHS1 itself (F4/R4) or to the Hyg$^R$ cassette (F4/R5). Finally, the HIS3 locus (bottom gel) was testing using a unique primer internal to the Cas9 gene and to the Kan$^R$ cassette (F5/R6). For optimal separation on the second and third DNA gels, a 2% agarose mixture was used compared to the standard 1% concentration. Molecular markers provide the nearest size (kilobases) for each independent gel. Finally, the expected fragment sizes for each diagnostic PCR are shown for each reaction. (B) An identical analysis was performed using the GFY-2003 parental strain that contained 6 [u1] sites flanking the same three loci. A PCR reaction of the entire HIS3 locus was performed (F6/R7) to illustrate complete replacement of the Cas9 expression cassette with the repaired HIS3 gene. At least one of the two primers used in each diagnostic PCR were designed outside the region used within the PCR reactions to amplify the integrated products. Three representative isolates from each parental lineage were also fully sequenced at the CDC11, SHS1, and HIS3 loci. For strain GFY-2002, the flanking [u2] sites remaining were confirmed by sequencing at the HIS3 locus. Diagnostic PCRs and sequencing of surviving colonies from control trials (FIG. 2B, Experiments B-E) can be found in FIG. 9.

FIG. 7. Integration at either two of three genomic loci (including removal of Cas9 itself), using a single sgRNA [u1] system and only 30 base pairs of flanking homology. (A) The GFY-2002 yeast strain was induced for Cas9-expression and transformed with the sgRNA[u1] vector and two PCR products for the CDC1 and SHS1 loci (also described in FIG. 2). Each PCR fragment had exactly 30 bps of homology to the genomic target available for homologous recombination. 10 representative clonal isolates were chosen (based on their tested growth profiles) and were analyzed by diagnostic PCR and visualized on DNA agarose gels. Chromosomal DNA was purified and diagnostic PCRs were performed to ascertain status at each manipulated locus and compared to DNA from the parental strain. For CDC11 (top three gels), the entire locus was amplified (oligos F7/R1) as well as small fragments flanking either the upstream [u1] site (F2/R2) or the downstream [u1] site (F3/R3) to determine if the 24 base pair Cas9 target site was still present or not. For SHS1 (fourth and fifth gels), a PCR (F8/R4) was performed with a unique primer internal to the SHS1 coding region that was not present within the parental strain as well as a PCR containing a unique primer to the Hyg$^R$ cassette that was present in the parental strain but not any putative integrant that repaired the SHS1 gene. Finally, the HIS3 locus was tested with a unique primer internal to the Cas9 gene and to the HIS3 3' UTR (F9/R6) to illustrate this genomic site was unperturbed since it was programmed with flanking [u2] sequences. For optimal separation on the second and third DNA gels, a 2% agarose mixture was used compared to the standard 1% concentration. Molecular markers, DNA size (kilobases). Finally, the expected fragment size for each diagnostic PCR is shown for each reaction. (B) An identical analysis was performed using the GFY-2003 parental strain (which has [u1] sites flanking the Cas9 cassette at the HIS3 locus). 6 independent clonal isolates were tested as in A with one difference: reactions also included a PCR of the WT HIS3 gene (also with 30 bps of flanking UTR) to simultaneously target and replace the endogenous Cas9 cassette. A PCR reaction of the entire HIS3 locus was performed (F10/R7) to illustrate complete replacement of Cas9 with the repaired HIS3 gene. At least one of the two primers used in each diagnostic PCR were designed outside the region used within the PCR reactions to amplify the integrated products.

FIG. 8. Possible outcomes of incomplete Cas9-targeting of [u1] sites at the CDC11 locus in vivo. While the majority of the tested isolates displayed proper replacement of the [u1]-flanked CDC11 locus with PCR-amplified WT CDC11 gene, a small percentage of isolates tested showed replacement of the downstream [u1] site but not the upstream [u1] site (see FIG. 3). The CDC11 locus replacement also differed from that of SHS1 and HIS3 (only for parental strain GFY-2003) in that the genomic target had an identical sequence as the amplified WT gene to be knocked-in. For SHS1, the WT gene replaced the Hyg$^R$ deletion, and for HIS3, the WT gene replaced the Cas9 cassette. If Cas9 targeted one or both of the [u1] sites at the CDC11 locus and the crossover event occurred outside of the coding sequence (top three panels), then the full WT CDC11 gene would replace the parental [u1]-flanked cassette and neither Cas9 target site would remain. This accounted for between 70-100% of screened isolates from four independent experiments. If Cas9 failed to create any DSBs at the CDC11 locus, then both [u1] sites would remain present; however, none of the isolates screened displayed this pattern. If Cas9 only targeted one [u1] genomic location at the CDC11 locus, and the crossover occurred within the CDC11 coding region, then the DSB would be repaired by the amplified WT copy, but would leave the additional [u1] intact. Between the upstream and downstream [u1] sites, only the upstream site remained; 100% of the downstream [u1] sites in all isolates tested (36) were properly replaced.

Finally, a collection of the control strains (FIG. 2, Experiments B-E) that were missing one or more PCR fragments for integration, yet were still viable, albeit rare, were tested by growth (Table 5) and diagnostic PCR (FIG. 9). Overall, the majority of surviving colonies did not have any of the proper allele(s) integrated and likely escaped Cas9-induced DSBs. Several isolates were found to integrate one PCR fragment, but failed to remove additional [u1] sites and the corresponding cassettes at those loci. However, two isolates tested from strain GFY-2002 had the CDC11 PCR fragment introduced but no SHS1 product, displayed a rare combination of proper integration of the CDC11 allele, excision of the shs1Δ::Hyg$^R$ cassette by the [u1] sites, and recombination via non-homologous end joining (NHEJ) (FIG. 9A, isolates 1 and 2). Previous work has shown NHEJ to be extremely inefficient in budding yeast (RATTRAY et al. 2001; DALEY et al. 2005; STORICI et al. 2006) and DNA repair via HR is orders of magnitude more efficient when a DSB is introduced (STORICI et al. 2003).

TABLE 5

Growth results for colonies from control experiments missing at least one PCR product.

| Parental Strain | PCR(s) | SD-URA | SD-HIS | G418 | Hyg | Total Colonies |
|---|---|---|---|---|---|---|
| 2002-B | CDC11 | + | − | + | − | 7 |
|  |  | + | − | + | + | 9 |
| 2002-C | SHS1 | + | − | + | − | 2 |
|  |  | + | − | + | + | 7 |
| 2002-D | — | + | − | + | − | 0 |
|  |  | + | − | + | + | 3 |
| 2003-B | CDC11/SHS1 | + | − | + | − | 0 |
|  |  | + | − | + | + | 6 |
| 2003-C | CDC11/HIS3 | + | − | + | − | 2 |
|  |  | + | − | + | + | 7 |
| 2003-D | SHS1/HIS3 | + | − | + | − | 0 |
|  |  | + | − | + | + | 6 |
| 2003-E | — | + | − | + | − | 0 |
|  |  | + | − | + | + | 6 |

Clonal isolates were pooled from multiple experimental trials using either 500 bps of flanking homology (FIG. 2) or 30 bps flanking homology (FIG. 7) and replica-plated onto various growth conditions (SD-URA, SD-HIS, YPD+G418, and YPD+Hygromycin). A "+" score indicates growth whereas "−" designates complete sensitivity. For most genotypes, two growth patterns were seen and the number of colonies displaying each pattern were totaled (far right column). Yeast were also tested on SD-LEU media for the presence or absence of the high-copy pRS425::sgRNA[u1] vector. After only two rounds of selection on SD-URA (no selective pressure for the LEU2 marker), 40/55 strains had lost the sgRNA-expressing plasmid. Representative isolates were taken from each category for further analysis by diagnostic PCR.

The letter designation (B, C, D, or E) in the parental strains of Table 5 is the same labeling as from FIG. 2 and from the same experimental setup. For the 2002-B experiment, the SHS1 PCR was not added. For 2002-C, CDC11 was omitted and for 2002-D, no PCR reactions were added to the yeast transformation. For parental strain 2003, at least two PCR products were added: 2003-B omitted the HIS3 product, 2003-C omitted the SHS1 product, 2003-D omitted the CDC11 product, and 2003-E had no PCRs added. The PCR products that were added to the reaction are listed. For simplicity, only combinations of two PCR products (2003-B) (omitting a third) were tested for strain GFY-2003, rather than all possible combinations.

FIG. 4. A model for Cas9-mediated gene manipulation by multiplexing of the genomic target site rather than multiplexing the guide RNA. (A) A schematic for traditional targeting of Cas9 to multiple genomic loci (including one locus where Cas9 is integrated); each locus is illustrated with two separate target sites for a total of 8 unique sgRNA cassettes requiring construction on one or more vectors. Additionally, at least one target site is modeled within the coding sequence of each gene (also see FIG. 5). Therefore, the three PCR products of Genes(1-3) requiring integration will also require their coding sequence to be altered to not include any of the overlapping genomic target sites. Finally, for manipulation of any essential genes (e.g. Gene1), a counter-selectable plasmid expressing a WT copy will also need to be altered to not include the genomic target sites (FIG. 5). Target sites are restricted to those that exist within the loci of interest; limitations of available PAM sites, or suboptimal (with potential off-target sites within the genome) sites may also limit target site positioning. (B) A novel approach to multiplexing the target site(s) rather than the guide RNA has a number of advantages over a traditional approach. First, the target site may be any stretch of 23 nucleotides from any known species (or completely unique) and can be specifically programmed to (i) greatly reduce and/or eliminator off-target effects within the genome being targeted and (ii) may be placed precisely within the target locus, down to the base pair, to optimally facilitate recombination and provide additional control over placement of the DSB(s) in vivo. While creation of the parental strain (and introduction of the target sites at multiple loci) is the limiting step, subsequent and repeated integrations at one or more loci would allow for precise and rapid strain construction at multiple loci with only a single guide RNA. Moreover, removal of the Cas9-expression cassette could be coupled with manipulation of the other loci (right panel), or maintained within the genetic background for further genomic editing at additional loci, at which time it could be quickly excised and removed using a second, unique target sequence (left panel). Finally, since the identity of the target site(s) at each loci are distinct from the targeted genes themselves, no modification of either the covering vector (endogenous WT copy), nor any of the integrated PCR-amplified copies is required as compared to a traditional method. Both approaches in combination would allow for a more systematic, tunable, and accurate manipulation of multiple loci in vivo in any desired organism.

FIG. 9. Analysis of surviving (very rare) isolates for control experiments missing one or more PCR fragments for integration. (A) Clonal isolates from multiple experimental trials (FIG. 2B) were tested by both growth (all tested isolates; Table 5) and diagnostic PCR (1 to 4 isolates chosen from each growth category). A summary of the yeast strains used and the corresponding PCR product(s) added to each reaction are summarized (lower left). Primers flanking the CDC11 [u1] Cas9 sites (F2/R2 and F3/R3) were used to determine whether the WT CDC1 allele has been integrated (top two gels). For the SHS1 locus, PCRs with a unique primer to the SHS1 coding sequence (R4, third gel) or to the $Hyg^R$ cassette (R5, fourth gel) were used. However, isolates 1, 2, and 39 had neither the WT SHS1 gene nor the deletion cassette present; therefore, the entire SHS1 locus was amplified (F4/R11, fifth gel). PCR products corresponding to the amplified product where the full SHS1 locus has been deleted are expected to be 996 bps. Finally, the HIS3 locus was interrogated by PCR (F14/R7, sixth gel). Select PCR products were purified and sequenced. The deletion present at the SHS1 locus in isolates 1, 2, and 39 was found to contain a repaired, single Cas9 [u1] site (double asterisk). The nearest molecular marker is indicated (kilobases) and 1% or 2% (first and second gels) agarose gels were used. For products imaged on separate gels, the gel fragments are shown as separate images; all images were sized identically and were marked with both DNA ladders and the corresponding PCR obtained using the parental (GFY-2002 or GFY-2003) yeast strain and the same primer set. (B) Identical diagnostic PCRs and sequencing were performed from isolates from the GFY-2003 lineage.

Materials and Methods

Yeast Strains and Plasmids

All budding yeast strains used in this study can be found in Table 2. Standard molecular biology methods were used in this study. The introduction of the [u1] and [u2] Cas9 target sites was performed by first cloning vectors using in vivo ligation and homologous recombination harboring a single Cas9 site including the PAM sequence. As an example, a vector (pGF-V130) containing the 5' UTR of CDC11 was digested with a restriction enzyme (NotI) downstream of the promoter sequence and transformed with a PCR fragment of the CDC11 coding region amplified with oligonucleotides containing overhanging "tails" to insert the Cas9 [u1] target sequence in-frame. Two constructs, each with a single flanking [u1] site placed upstream or downstream of CDC11 were created separately and then combined by a second round of in vivo ligation to generate the final construct that contained both flanking [u1] sites as well as flanking CDC11 5' and 3' UTR (330 bps of each). This process was repeated for the shs1Δ::$Hyg^R$ cassette harboring flanking [u1] sites and two Cas9-expressing cassettes containing either [u1] or [u2] sites at the HIS3 locus (Table 2). The generated constructs were PCR amplified and integrated into the parent strain in successive yeast transformations. Diagnostic PCRs and Sanger sequencing (Univ. of California, Berkeley Barker Hall Sequencing Facility) of chromosomal DNA were performed to ensure proper integration of all manipulated loci.

Plasmids used in this study can be found in Table 4 Expression of the sgRNA cassettes was modeled after a previous study using the snoRNA SNR52 promoter and SUP4 terminator sequences and were synthesized as custom genes with flanking XhoI and BamHI restriction sites (GenScript, Piscataway, N.J.). The [u1] and [u2] sequences were chosen from two human genes, SEPT9 and MMP23A, respectively, using the DNA2.0 gRNA Design Tool (DNA2.0, Newark, Calif.). Putative guide sequences were then examined against the entire yeast genome using a nucleotide BLAST search (National Center for Biotechnology Information) and sequences were considered for having the lowest possible number of matches to the 15 base pair sequence (PAM+upstream 12 bps) important for Cas9 "seeding" to minimize off-target effects. Additionally, the chosen [u1] and [u2] sequences were checked against the backbone vector sequences of the pRS316 covering vector, the high-copy sgRNA-expressing pRS425/pRS423 vectors, and both the $Kan^R$ and $Hyg^R$ cassettes to ensure no highly similar matches existed in these exogenous non-yeast sequences.

Culture Conditions

Yeast were grown in rich YPD or YPGal medium (2% peptone, 1% yeast extract, 2% dextrose or 2% galactose), or in synthetic medium containing the necessary amino acids with either 2% dextrose or a 2% raffinose and 0.2% sucrose mixture. For transformation of yeast using the Cas9-mediated system, strains were grown overnight in synthetic medium with a raffinose/sucrose mixture lacking uracil (to select for the CDC11-expressing WT covering plasmid) to saturation, back-diluted into YPGal (to an $OD_{600}$ of approximately 0.25-0.35), and grown at 30° C. for 4.5-5.0 hours. A modified lithium acetate transformation protocol was used to transform 10 $OD_{600}$ of yeast with combinations of purified plasmid DNA and/or PCR products. Yeast were heat shocked for 45-50 minutes at 42° C. and recovered in fresh YPGal overnight at 30° C. prior to plating onto selective media (selection for both plasmids and no selection for integrated knock-in alleles). An identical transformation protocol was used whether Cas9 was integrated at the HIS3 locus or expressed on a CEN-plasmid.

The growth of single yeast colonies on various media (G418, Hygromycin, SD-HIS, etc.) were tested by first selecting isolated colonies, creating a small square "patch" (1 $cm^2$) on an SD-URA plate, incubating overnight at 30° C., and then replica-plating to additional plates to be scored after 1 additional day of incubation. For yeast plates containing a significant number of colonies, the total colony count was estimated in several ways. First, several sectors (½, ¼, or ⅛, etc.) were selected on the agar plate and the total number of colonies in the sample sector was counted and extrapolated to the entire surface area. Second, subsequent repeated experiments plated various dilutions (1/10, 1/20, 1/50, etc.) of the final transformation product and the total colony counts were added, extrapolated, and averaged together. All experiments were performed in at least triplicate.

Fluorescence Microscopy

For fluorescence microscopy, yeast were grown to saturation overnight in S+Raff/Suc-LEU, back-diluted into YPGal, grown for five hours at 30° C., harvested, washed with water, and prepared on a standard microscope slide with a coverslip. Samples were immediately imaged on an Olympus BH-2 upright fluorescence microscope (Olympus, Tokyo, Japan) with a 100× objective lens. A CoolSNAP MYO CCD camera (Photometrics, Tucson, Ariz.), a SOLA light source (Lumencore, Beaverton, Oreg.), Micro-Manager software, and ImageJ software (National Institute of Health) were used to process fluorescent images. The cell periphery was determined using an over-exposed fluorescence image.

Polymerase Chain Reaction (PCR) and DNA Sequencing

All PCR reactions were performed using either high fidelity KOD Hot Start DNA Polymerase (EMD Millipore, Billerica, Mass.) or PfuUltra II Fusion Hot Start DNA Polymerase (Agilent Technologies, Santa Clara, Calif.) according to the recommended manufacturer's conditions (KOD reactions all contained 3 mM $Mg^{2+}$) on a PTC-200 Thermal Cycler (MJ Research, Bio-Rad). Oligonucleotides (Integrated DNA Technologies, Coralville, Iowa) used in this study can be found in Table 6. For PCR reactions used in the Cas9-mediated integrations, the template DNA was from either purified yeast chromosomal DNA or from bacterial-based plasmids (that cannot be propagated in yeast). Products for integration were confirmed to be the correct size on an agarose gel, but were not purified nor gel extracted; amplified DNA was directly added to the yeast transformation reaction. For diagnostic PCRs to confirm various manipulated loci, DNA agarose gels (1% or 2%) containing Ethidium Bromide were used to separate and image (ChemiDoc System, Bio-Rad Laboratories, Hercules, Calif.) separated products. Sanger DNA sequencing was performed on all constructed vectors and plasmid intermediates. For sequencing of genomic loci, chromosomal DNA was isolated and PCR amplified using a high-fidelity polymerase. The product sizes were confirmed on an agarose gel and the remaining DNA was purified using a QIAquick PCR purification kit (Qiagen, Valencia, Calif.) and sequenced with overlapping coverage at each desired locus.

TABLE 6

Oligonucleotides used in this study.

| Oligo-nucleotide | Description | Sequence (5' to 3') |
|---|---|---|
| F1 | CDC11 UTR[1] +406 F | CATCTACAAAAGCAGGTTATAGCTC CGTTAAAC (SEQ ID NO: 1162) |
| F7 | CDC11 UTR +330 F | CACAACATGGAACATAACATTTAAA CATCGTTCTCAATC (SEQ ID NO: 1163) |
| R1 | CDC11 UTR -327 R | GCTAAGTGATGTTCTGGTCTTTCCAA AATTCTC (SEQ ID NO: 1164) |
| F2 | CDC11 UTR +101 F | GATCGAAAAGTAAAATAGGTAGAC ACCACGTATTG (SEQ ID NO: 1165) |
| R2 | CDC11 Int +75 R1 | CACAGTGAAGGTTATACCTCTTTTCA AATGCTTTC (SEQ ID NO: 1166) |
| F3 | CDC11 Int +1233 F | GAAGCCAGGTTGGAAAAAGAGGCG AAAATC (SEQ ID NO: 1167) |
| R3 | CDC11 UTR -89 R | TAATATACCAGATGTATTTACTTATA TACAACACTCACTC (SEQ ID NO: 1168) |
| F4 | SHS1 UTR +800 F | CATTACTAGAGTTTGCTGGTGTTGCA GATCG (SEQ ID NO: 1169) |
| F8 | SHS1 UTR +500 F | GTTCCTCCGGTTTAAACTGATCCATA GTGATAG (SEQ ID NO: 1170) |
| R4 | SHS1 Int +999 R | ACGGTAATTCTCGTAAAGCAAATTT TGCGTGG (SEQ ID NO: 1171) |
| R5 | Int Hyg R | CTCCTACATCGAAGCTGAAAGCACG AG (SEQ ID NO: 1172) |
| F5 | Cas9 Int +2903 F | CTGAAGTCTAAGCTGGTCTCAGATT TCAGAAA (SEQ ID NO: 1173) |
| F9 | Cas9 Int +3477 F | GTGGAGAAAGGGAAGTCTAAAAAA CTCAAAAGC (SEQ ID NO: 1174) |
| R6 | Int Kan R | GAACACTGCCAGCGCATCAACAATA TTTTC (SEQ ID NO: 1175) |
| F6 | HIS3 UTR +992 F | GGGTCAGTTATTTCATCCAGATATA ACCCG (SEQ ID NO: 1176) |
| F10 | HIS3 UTR +500 F | TTCTCGACGTGGGCCTTTTCTTGCC ATAT (SEQ ID NO: 1177) |
| R7 | HIS3 UTR -497 R | GTAACCACCACGACGGTTGTTGCTA AAGAA (SEQ ID NO: 1178) |
| F11 | CDC11 UTR +30 F | CACAAGGCCTAAAGTTGCTAACCAC CAGCCATGTCCGGAATAATTGACGC ATCTTCTGCA (SEQ ID NO: 1179) |
| R8 | CDC11 UTR -30 R | AAGAAATAAGTGAGGAAGCCAAAA GCGGACTCATTCTTCCTGTTTGATTT TCGCCTCTTTTTCC (SEQ ID NO: 1180) |
| F12 | SHS1 UTR +30 F | TATAATTGCTAGAAAAATATATTAT TAATCATGAGCACTGCTTCAAC (SEQ ID NO: 1181) |
| R9 | SHS1 UTR -30 R | GCTCAGCTTTGGATTTTGTACAGATA CAACACTGGATGGCGGCGTTAGTAT CGAATC (SEQ ID NO: 1182) |
| F13 | HIS3 UTR +30 F | AATGAGCAGGCAAGATAAACGAAG GCAAAG (SEQ ID NO: 1183) |
| R10 | HIS3 UTR -30 R | GTATGCTGCAGCTTTAAATAATCGG TGTCA (SEQ ID NO: 1184) |

TABLE 6-continued

Oligonucleotides used in this study.

| Oligo-nucleotide | Description | Sequence (5' to 3') |
|---|---|---|
| F14 | Int Kan F | CGGTTGCATTCGATTCCTGTTTGTAA TTGTCC (SEQ ID NO: 1185) |
| R11 | SHS1 UTR -469 R | CCACTAGAGCATTGGCAGAATTATA TGGTAGT (SEQ ID NO: 1186) |

"UTR+/−" in Table 6 designates upstream 5' or downstream 3' sequence to the specified gene. "Int" designates a position internal to the coding sequence of the specified ORF.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11248216B2). An electronic copy of the "Sequence Listing" will also be available from the USPTO upon request and payment of the fee set forth in 37 CFR 1.19(b)(3).

What is claimed is:

1. A genetically modified cell,
   wherein the genetically modified cell is genetically modified with a first heterologous nucleic acid that: (i) is integrated into one or more positions within the genetically modified cell's genome, (ii) comprises a first CRISPR/Cas target sequence, and (iii) has a length in a range of from 17 to 40 nucleotides (nt),
   wherein the first CRISPR/Cas target sequence is adjacent to a protospacer adjacent motif (PAM) at each position the first heterologous nucleic acid is integrated, and
   wherein said first CRISPR/Cas target sequence is not present in the genome of the parent cell used to make the genetically modified cell.

2. The genetically modified cell of claim 1, wherein the genetically modified cell is a eukaryotic cell.

3. The genetically modified cell of claim 1, wherein said first heterologous nucleic acid is:
   a) integrated into a position that is within a protein-coding sequence, an RNA-coding sequence, or a transcription control element; or
   b) integrated into two or more positions within the genome.

4. The genetically modified cell of claim 3, wherein at least two of the two or more positions: (i) are within protein-coding sequences, RNA-coding sequences, or transcription control elements; or (ii) flank a protein-coding sequence, an RNA-coding sequence, or a transcription control element.

5. The genetically modified cell of claim 4, wherein said first heterologous nucleic acid is integrated into, or flanks, two or more different protein-coding sequences, RNA-coding sequences, or transcription control elements.

6. The genetically modified cell of claim 1, wherein the genetically modified cell comprises a CRISPR/Cas endonuclease and/or a nucleic acid comprising a nucleotide sequence encoding the CRISPR/Cas endonuclease.

7. The genetically modified cell of claim 6, wherein the CRISPR/Cas endonuclease is a Cas9 protein.

8. The genetically modified cell of claim 6, wherein the nucleotide sequence encoding the CRISPR/Cas endonuclease is operably linked to a promoter.

9. The genetically modified cell of claim 6, wherein the genetically modified cell comprises said first heterologous nucleic acid integrated into:
   (i) a position within, or two positions that flank, a nucleotide sequence encoding the CRISPR/Cas endonuclease, or
   (ii) a position within, or two positions that flank, a transcription control element that is operably linked to a nucleotide sequence encoding the CRISPR/Cas endonuclease.

10. The genetically modified cell of claim 1, wherein the genetically modified cell is genetically modified with a second heterologous nucleic acid comprising a second CRISPR/Cas target sequence that is different than said first CRISPR/Cas target sequence.

11. The genetically modified cell of claim 1, comprising:
    (i) a CRISPR/Cas guide RNA comprising a guide sequence that is complementary to the first CRISPR/Cas target sequence, and/or
    (ii) a nucleic acid encoding said CRISPR/Cas guide RNA.

12. A kit comprising:
    (i) a plurality of genetically modified cells according to claim 1, wherein each cell of the plurality of cells comprises said first heterologous nucleic acid integrated into one or more different positions within the genome; and (ii) a CRISPR/Cas guide RNA, or a nucleic acid encoding said CRISPR/Cas guide, wherein the CRISPR/Cas guide RNA comprises a guide sequence that is complementary to the second CRISPR/Cas target sequence.

13. A method of generating the genetically modified cell of claim 1, the method comprising:
    incorporating the first heterologous nucleic acid into one or more positions within a parent cell's genome, thereby generating the genetically modified cell of claim 1.

14. The method according to claim 13, comprising incorporating the first heterologous nucleic acid into
    (i) a position within, or two positions that flank, a nucleotide sequence encoding a CRISPR/Cas endonuclease, or
    (ii) a position within, or two positions that flank, a transcription control element that is operably linked to a nucleotide sequence encoding a CRISPR/Cas endonuclease.

15. The method according to claim 13, wherein the method comprises incorporating a second heterologous nucleic acid that comprises a second CRISPR/Cas target sequence that is different than the first CRISPR/Cas target sequence, into one or more positions within the parent cell's genome.

16. The method according to claim 13, comprising incorporating a nucleotide sequence encoding a CRISPR/Cas endonuclease into the parent cell's genome.

17. The method according to claim 16, wherein the CRISPR/Cas endonuclease is a Cas9 protein.

18. A method of editing the genome of the genetically modified cell of claim 1, the method comprising:
    introducing into the genetically modified cell a CRISPR/Cas guide RNA, or a nucleic acid encoding said CRISPR/Cas guide RNA, wherein the CRISPR/Cas guide RNA comprises a guide sequence that is complementary to the first CRISPR/Cas target sequence.

19. The method of claim 18, further comprising introducing into the genetically modified cell a CRISPR/Cas endonuclease, or a nucleic acid encoding said CRISPR/Cas endonuclease.

* * * * *